(12) United States Patent
Young et al.

(10) Patent No.: US 8,252,851 B2
(45) Date of Patent: Aug. 28, 2012

(54) FORMULATIONS AND COMPOSITES WITH REACTIVE FILLERS

(76) Inventors: Anne Margaret Young, London (GB); Sze Man Ho, London (GB)

( * ) Notice: Subject to any disclaimer, the term of this patent is extended or adjusted under 35 U.S.C. 154(b) by 385 days.

(21) Appl. No.: 12/443,049

(22) PCT Filed: Sep. 26, 2007

(86) PCT No.: PCT/GB2007/003662
§ 371 (c)(1),
(2), (4) Date: Mar. 26, 2009

(87) PCT Pub. No.: WO2008/037991
PCT Pub. Date: Apr. 3, 2008

(65) Prior Publication Data
US 2010/0069469 A1    Mar. 18, 2010

(30) Foreign Application Priority Data
Sep. 26, 2006    (GB) .................................. 0618963.3

(51) Int. Cl.
*C08J 3/00* (2006.01)
(52) U.S. Cl. ........................................ 523/116; 523/115
(58) Field of Classification Search .................... 523/116
See application file for complete search history.

(56) References Cited

U.S. PATENT DOCUMENTS

| | | | | |
|---|---|---|---|---|
| 4,324,592 | A * | 4/1982 | Patel et al. | 106/691 |
| 6,214,368 | B1 * | 4/2001 | Lee et al. | 424/423 |
| 6,331,312 | B1 * | 12/2001 | Lee et al. | 424/426 |
| 6,387,981 | B1 * | 5/2002 | Zhang et al. | 523/117 |
| 6,642,285 | B1 * | 11/2003 | Bohner | 523/115 |
| 6,730,715 | B2 * | 5/2004 | Jia | 523/115 |
| 6,949,251 | B2 * | 9/2005 | Dalal et al. | 424/423 |
| 6,994,726 | B2 * | 2/2006 | Lin et al. | 623/16.11 |
| 7,118,705 | B2 * | 10/2006 | Lin et al. | 264/333 |
| 7,150,879 | B1 * | 12/2006 | Lee et al. | 424/422 |
| 7,211,136 | B2 * | 5/2007 | Jia et al. | 106/35 |

(Continued)

FOREIGN PATENT DOCUMENTS

CA    2015081    10/1990

(Continued)

OTHER PUBLICATIONS

Leung, D. et al., "Chlorhexidine-releasing methacrylate dental composite materials," Biomaterials (2005) 26:7145-7153.

(Continued)

*Primary Examiner* — James J Seidleck
*Assistant Examiner* — Peter A Salamon
(74) *Attorney, Agent, or Firm* — Valauskas Corder LLC

(57) ABSTRACT

The invention provides composite materials prepared by i) providing a fluid formulation comprising (1) at least one compound capable of polymerization and/or cross-linking and (2) a water-consuming reactive filler; ii) optionally injecting said formulation into a site of use; iii) polymerising and/or cross-linking said compound, to form a solid polymer matrix (which may be degradable or non-degradable); iv) causing or allowing said filler to react with water absorbed by said polymer matrix, to produce a solid filler material which is dispersed throughout the composite material. The hydration and formation of the solid filler in situ provides desirable properties to the composites, which have utility for dental composites, bone fillers and adhesives and so on. The composite may also be used to release an active ingredient e.g. an antibacterial or DNA.

23 Claims, 18 Drawing Sheets

U.S. PATENT DOCUMENTS

| | | | |
|---|---|---|---|
| 7,264,825 B2 * | 9/2007 | Vogt et al. | 424/489 |
| 7,331,789 B2 * | 2/2008 | Karmaker et al. | 433/220 |
| 7,407,542 B2 * | 8/2008 | Lemaitre et al. | 106/35 |
| 2003/0083400 A1 * | 5/2003 | Jia | 523/116 |
| 2004/0244651 A1 * | 12/2004 | Lemaitre et al. | 106/690 |
| 2009/0048145 A1 * | 2/2009 | Hellerbrand et al. | 514/2 |
| 2010/0112028 A1 * | 5/2010 | Hellerbrand et al. | 424/423 |

FOREIGN PATENT DOCUMENTS

| | | |
|---|---|---|
| DE | 19930335 | 1/2001 |
| EP | 0394798 | 10/1990 |
| EP | 0797975 | 10/1997 |
| EP | 1066813 | 1/2001 |
| EP | 1142596 | 10/2001 |

OTHER PUBLICATIONS

International Search Report and Written Opinion for Application No. PCT/GB2007/003662 dated Jan. 15, 2008 (11 pages).

* cited by examiner a)

b)

c)

d)

a)

b)

c)

d)

e)

a)

b)

c)

d)

| Code | $m_{calc}$ | LA$_{tot}$ / PG | | End groups / PG | | | | Total molecular weight (g/mol) |
|---|---|---|---|---|---|---|---|---|
| | | mol/mol | % | LA$_e$ (mol/mol) | % | MA (mol/mol) | % | |
| P34L8DMA | 6.9 | 0.44 | 95 | 0.056 | 95 | 0.024 | 40 | 3161 |
| P34L2DMA | 3.3 | 0.11 | 95 | 0.040 | 68 | 0.048 | 81 | 2413 |
| P17L4DMA | 4.7 | 0.43 | 92 | 0.085 | 72 | 0.096 | 81 | 1671 |
| P7L8DMA | 8.2 | 1.72 | 79 | 0.23 | 82 | 0.18 | 65 | 1449 |
| P7L2DMA | 3.4 | 0.50 | 92 | 0.17 | 59 | 0.25 | 88 | 845 | a) b)

c)

a)

b)

c)

(d)

a)

b)

a)

b)

US 8,252,851 B2

FORMULATIONS AND COMPOSITES WITH REACTIVE FILLERS

CROSS-REFERENCE TO RELATED APPLICATIONS

This patent application is a national stage filing under 35 U.S.C. 371 of International Application No. PCT/GB2007/003662, filed on Sep. 26, 2007, which claims foreign priority benefits to United Kingdom Patent Application No. 0618963.3, filed on Sep. 26, 2006. These applications are incorporated herein by reference in their entireties.

TECHNICAL FIELD

This invention relates to formulations, suitable for use as adhesives and fillers in biomedical applications, to composites formed from these formulations, and to uses of these formulations and composites. Additionally, the invention relates to formulations and composites suitable for use as delivery systems for active agents, such as drugs or DNA molecules.

BACKGROUND OF THE INVENTION

Materials which are initially liquid and mouldable but that can set rapidly in situ giving immediate structural support and adhesion to surrounding tissues are of great value in bone tissue-engineering applications as well as dental, maxillofacial and orthopaedic surgeries. As they set from liquid to solid, micromechanical bonds are formed with the surrounding surfaces. The adhesive effect is especially strong with rough surrounding surfaces.

Setting of such materials may, for example, be initiated by chemical initiators or by exposure to visible or UV light (especially in cases of chemical polymerisation and cross-linking, such as in double bond containing (eg. methacrylate) polymeric formulations), or may be a result of other chemical reactions upon mixing of two components (eg acid/base in glass ionomer dental and brushite-forming bone cements) or solvent removal or evaporation from the initial liquid formulation.

For example, injectable methacrylate based dental restorative composites and adhesives and poly(methyl methacrylate) (PMMA) bone cements have been widely used for applications such tooth restoration and for fixing of orthopaedic implants. After injection of the initially fluid formulation (containing various methacrylate monomers and inorganic particles or PMMA powder in combination with liquid methyl methacrylate monomer), curing occurs, due to the presence of chemical initiators, and results in a solid material. Antibiotics or other antibacterial agents may be incorporated into dental composites or PMMA bone cements to decrease the risk of infection. Release of these agents is likely to decrease with time as it is controlled by diffusion which may be enhanced by water sorption At present, however, there are functional limitations with all commercialised bone repair and tooth restoration products. The PMMA cements and dental restoratives discussed above are strong, but curing of large volumes generates excessive heat and material shrinkage which may cause necrosis of surrounding tissue or debonding. Additionally, if setting is slow, release of potentially toxic monomers is a problem [20-21]. PMMA also causes potential long-term biocompatibility problems, as it does not degrade in the body. [22]

With tooth restoration the composite is preferably permanent as natural repair is limited.

Since bone can regenerate, materials for bone repair should, however, if possible slowly degrade to components that may be used for tissue renewal or safely eliminated. The materials can also potentially be used simultaneously as small or large (eg DNA or protein) drug molecule controlled delivery reservoirs. If the material erodes at a constant rate from the surface then it may be possible to have linear (as opposed to declining) release of the drug at a rate commensurate with the device erosion.

Biodegradable orthopaedic fixation devices have been fabricated from various polyesters including poly lactide, glycolide or caprolactone. Polylactide screws have been shown to be useful alternatives to metal screws and implants [23].

Polylactides and polyesters are not generally injectable (although by raising the temperature above their glass transition temperature some formulations can become sufficiently fluid for moulding into a large cavity). Using polyethers as catalysts for ring-opening polymerisation of lactides, however, it is possible to produce fluid, relatively short chain poly(ether-co-ester)s. Attachment of acrylate or methacrylate end-groups then produces monomers which can cross-link and set with light or chemical cure activation. [Refs 24,25] Other injectable crosslinkable materials, including polyanhydrides [26] and polypropylene fumarates [Ref 27] have also been produced.

A problem with these materials is that controlling the rate of degradation (and hence concomitant drug release, where applicable) and mechanical properties, whilst maintaining rapid controllable set, is difficult to achieve [4-9].

A further problem, especially with more hydrophilic polyesters, can be that degradation is catalysed in the core of the material, leading to sudden catastrophic degradation instead of steady controlled surface degradation [10]. Surface degradation can be achieved through raising polymer hydrophobicity or polymer hydrolytic lability, but the need to maximise linear degradation can limit feasible polymer structures and thereby other material properties.

One method of improving control over mechanical and many other properties of polymers is through the addition of inorganic particles. In dental composites for example inorganic particles, such as silica glass, are added to methacrylate polymers to improve control over mechanical properties. The interface between the polymer and inorganic component is, however, often a point of material weakness. To overcome this problem the fillers are generally bound to the polymeric matrix phase via surface silane coupling agents but this interface may be weakened by water sorption catalysed hydrolysis of the silane [11].

As the filler loading is raised mechanical properties can improve but the viscosity of the fluids increases until, above the wet point of the filler, the formulation becomes too dry and crumbles. Smaller particles generally reduce wear and improve mechanical properties [23] but as the particles become smaller than about 5 µm, the maximum possible filler loadings (or filler/formulation wet points) can substantially decline, due to increased repulsions at the particle/matrix interface.

Filler addition to methacrylates is also known to reduce heat and shrinkage of polymerisation and to raise modulus, but can reduce the light-activated polymerisation rate in thicker samples, due to scattering effects [32, 33].

An alternative to polymeric adhesives and fillers is the use of calcium phosphate cements (CPCs). These are generally considered to be more biocompatible than the polymers and are widely used e.g. in craniofacial surgery and dental applications [28, 29]. For example, cements that form of hydroxyapatite (HA, $Ca_{10}(PO_4)_6(OH_2)$— the primary mineral component of bone, enamel and dentine) have been developed. One example involves reaction between tetracalcium phosphate and anhydrous dicalcium phosphate $$2CaHPO_4 + 2Ca_4(PO_4)_2O \rightarrow Ca_{10}(PO_4)_6(OH)_2$$

Upon mixing these phosphates with water, hydroxyapatite can slowly form. As the product crystallizes, it takes on a putty-like consistency and can be implanted or injected and contoured to a defect. The cement then completes the process and hardens, typically within ten to fifteen minutes, securing its position within the defect.

Faster setting aqueous calcium phosphate cements have also been developed using mixtures of monocalcium phosphate monohydrate (MCPM) and tricalcium phosphate ($\beta$-TCP). These two phosphates combine rapidly when mixed with water to form lower density dicalcium phosphate dihydrate (DCPD, also known as brushite) according to the expression (Refs 18-19).

$$\beta\text{-}Ca_3(PO_4)_2 + Ca(H_2PO_4)_2 \cdot H_2O + 7H_2O \rightarrow 4CaHPO_4 \cdot 2H_2O \qquad (1)$$

In these cements the MCPM particles dissolve in water, then re-precipitate, solidifying the cement and forming brushite (DCPD) or monetite (dicalcium phosphate anhydrous (DCPA)) crystallites. In the body these may be slowly transformed to hydroxyapatite required for reminearalisation of bone. An excess of water is required in these cements to provide initial fluidity, and so the final materials have significant porosity thereby limiting mechanical properties and applications.

Degradation of calcium phosphate cements releases calcium and phosphate ions, which may be needed by the body to grow new bone tissue. However, disadvantages include brittleness, lack of strength and slowness of set. Although acting as effective adhesives and fillers, they generally do not provide significant support. They are also not generally useful as prolonged drug delivery devices, since drugs incorporated in the cement can be released too quickly because of the high porosity [30].

Combinations of polymers and calcium phosphates have been studied previously [44-48]. For example, various calcium and phosphate-containing particles, including phosphate based glasses, hydroxyapatite and tricalcium phosphate, have been added to degradable polymers (Refs 12-17). However, high filler loading can be restricted and, without strong interaction/bonding between the matrix polymer and inorganic phases, the interface can be a point of material weakness.

Numerous studies have shown that the addition of phosphate based inorganic particles to conventional polyesters can modify degradation and mechanical properties and also buffer acidic degradation products. However hydrophilic particle addition can be detrimental to dimensional stability, due to excessive water sorption-induced swelling.

Hydroxyapatite has previously been shown to increase the modulus of some degradable polymer composites, but the effect is rather limited (40). Additionally, hydroxyapatite formed by high temperature routes is of low solubility at pH 7 and so would be very slow to degrade (if at all) in the body. Large hydroxyapatite crystals would therefore be unlikely to provide the calcium and phosphate ions required for bone tissue regeneration.

Some acidic polymers (eg. polyacrylic acid) have also previously been added to calcium phosphate cements in an attempt to improve compressive strength, drug release characteristics and durability, but water remains the initial main continuous phase of the cement and is required in excess to give sufficient working time of the fluids. This limits the mechanical properties that may be achievable. [34,35] In addition these cements will still not have the rapid and controllable set possible with light curable methacrylates. With slow setting especially hydrophilic cements it is difficult to prevent drug "dumping" in the body before full set is achieved.

DESCRIPTION OF THE INVENTION

The present invention now provides formulations containing reactive fillers, which successfully combine advantages of injectable polymer formulations with those of the calcium phosphate cements.

In preferred embodiments, these fillers may impart many advantages to the composite materials produced from the formulations, such as increased surface hardness, increased modulus, and improved dimensional stability and biocompatability. In addition, the degradation and drug release properties of the composites may be better controlled.

Without wishing to be bound by theory, it is believed that the polymer composites of the invention have improved properties, compared to composites of conventional polymers and non-reactive fillers, due to better mixing between the inorganic particles and the polymer matrix phase. The reaction of the components may also provide a mechanism to increase the set or hardness of the initially fluid formulations and additionally bind water absorbed by the polymers, reducing potential plasticisation.

That solid reactive fillers can perform their water-consuming function in situ in a solid polymer matrix, and thereby enhance the properties of the resulting composite is quite unexpected. In particular, the observation that this reaction can proceed to completion in some formulations purely upon water sorption by the surrounding polymer is somewhat surprising. In addition, the fact that water sorption could encourage release of some drugs before the water is bound to the inorganic fillers can be an added benefit if drug release is highly restricted.

Fluid Formulations

Accordingly, an aspect of the present invention provides a fluid formulation (which may be used in producing the composites of the invention), comprising at least one compound capable of polymerising and/or cross-linking to form a solid polymer matrix, and a water-consuming reactive filler; wherein said filler is capable of reaction with water absorbed by the set polymer matrix, to produce a solid material, wherein said solid material is dispersed through the polymer matrix.

By 'fluid formulation' is meant a fluid composition having a viscosity low enough to enable it to be injected into a site of use. As will be readily appreciated by one skilled in the art, in light of the following description, the viscosity required may depend upon the exact site and mode of application. For example with larger cavities with easy access, putty-like consistencies may be suitable. More liquid formulations (~1 to 100 mPas) may spread better over the tissue, however, providing better adhesion. If the material is to be injected through a fine needle then the viscosity must be reduced. This viscosity may be reduced by lowering the level of filler.

'Cross-linking', 'polymerisation', 'curing' or 'setting' refers to the solidification process, by which the initially fluid formulation forms a solid 3-dimensional polymeric network or 'matrix'. This may be achieved by chemical reaction, i.e. the formation of covalent or ionic bonds between monomers ('polymerisation'; oligomerisation) or between polymeric chains (chemical 'cross-linking'), or may be by physical interactions between polymeric chains (such as occurs in the formation of crystalline regions) in a three dimensional network structure. The term 'cross-linking', as used herein, may refer to chemical cross-linking or physical cross-linking. Chemical cross-linking and/or polymerisation may be achieved by means including heat ('thermal curing'), UV or visible light ('photo curing') or mixing with a chemical initiator ('chemical curing'). Solidification may also occur by physical cross-linking, which may, for example, be due to removal or evaporation of solvent from a fluid composition or fluid polymer-containing liquid, or due to a change of temperature.

The 'water-consuming reactive filler' is an inorganic compound, or a mixture of inorganic compounds, which is incorporated into the fluid formulation. Usually the fillers will be of a solid particulate nature and between 0.5 and 200 micron in diameter. The fillers used in the present invention are capable of undergoing a chemical reaction within the solid polymer matrix, which reaction may alter the chemical and physical properties of the particles, and which may preferably result in the formation of new chemical species. The solid material formed from this precipitation may have a lower density than that of the starting compound(s), due to the extra water content, and hence may require a larger volume. The precipitated material may therefore be forced to disperse through the 3-D matrix, resulting in smaller particles being formed than were originally present.

As described below, the formulations according to the invention may be prepared by mixing solid particles comprising the water-consuming reactive filler with a fluid phase comprising the polymerisable/cross-linkable compound. The fluid phase may include solvents, such as ethyl acetate, acetone, alcohol, or water. If water is present as a solvent, it is preferably present in low quantities. Preferably there is less water present than would be required to fully react with all of the reactive water-consuming filler, more preferably there is less than 50%, 40%, 30%, 20% or 10% of this amount Most preferably water is not present in the fluid phase, i.e. it is non-aqueous. Nevertheless, in certain embodiments described below low levels of water may be present e.g. to aid dispersion of water miscible drug molecules such as DNA or proteins. In this case surfactants may be utilised to emulsify the water in the non-aqueous phase. Preferably the polymerisable/cross-linkable compound itself is a fluid and in this case, there may be no need to add any solvents—the compound itself forms the fluid phase and is preferably substantially free of water. In these cases, water is gained only after the polymer matrix is formed, via restricted water sorption.

Reaction of these fillers occurs in the presence of water, which has been absorbed into the polymer matrix, and this reaction consumes (traps) at least some, preferably at least 50%, 60%, 70% or 80%, more preferably at least 90%, most preferably 100%, of this absorbed water.

'Consumption' or 'trapping' of the absorbed water may, in some embodiments, involve a chemical reaction of the absorbed water molecules, in which at least one of the covalent bonds within the water molecule is broken and new chemical species are formed (new ions or molecules) therefrom. In other preferred embodiments, the water molecules may remain intact, but are incorporated in the crystal structure of the reaction product, i.e. in a hydrate.

Generally, the surfaces of the compound(s) making up the reactive filler particles initially dissolve in the water absorbed by the polymer matrix phase. Upon further water sorption by the polymer it may expand into any vacated particulate space. The dissolved inorganic particles can then undergo reaction with themselves and/or with the water to produce in situ a new solid compound (or mixture of compounds) which precipitates within the polymer. This may result in greater entangling of the polymer and inorganic phases, improved organic/inorganic component interaction and removal of non-bound, polymer-plasticizing water, and thereby an improvement in mechanical properties.

Example Fillers

In preferred embodiments the solid insoluble compound forms from a more soluble reactive filler. The reaction may proceed by an acid-base type reaction where there is transfer of small hydrogen ions which may diffuse readily through the polymer structure.

Preferably the water-consuming reactive filler comprises at least one calcium-containing compound, most preferably a calcium phosphate compound. Preferably there are two different such compounds. Preferably at least one of the reactive fillers should, be able to dissolve in water absorbed by the polymer, react and precipitate as a less soluble calcium phosphate species directly within the polymer before it can be extracted into any surrounding aqueous environment. In preferred embodiments of the present invention the reactive fillers are preferably tricalcium phosphate and monocalcium phosphate monohydrate and the final hydrated less water soluble products brushite or hydroxyapatite.

The term 'calcium phosphate' or 'calcium phosphate compound' refers to any inorganic compound containing calcium ions ($Ca^{2+}$) and phosphate ions, wherein the phosphate ions may be in the form of, for example, orthophosphates ($PO_4^{3-}$), metaphosphates ($PO_3^-$) or pyrophosphates ($P_2O_7^{4-}$) and which may also contain hydrogen or hydroxide ions.

Furthermore, in phosphate glasses there can be various other polyphosphate ions. In addition, other counterions may also be present. For example in phosphate glasses, calcium can be partially replaced by sodium or iron to increase or decrease its aqueous solubility respectively. Flouride ions can also be included to reduce the solubility of the final calcium phosphates. Silver ions may also be added to provide antibacterial action.

The calcium phosphate compounds may also be hydrates or solvates, i.e. may contain solvent molecules within their crystal structure. Preferably, however, the reacted less soluble calcium phosphate structures will contain more water than the reactants to reduce the effects of water on the surrounding polymer.

Examples of calcium phosphates include, but are not limited to: tricalcium phosphate $Ca_3(PO_4)_2$ (TCP, also called tribasic calcium phosphate—occurs in $\alpha$ and $\beta$ phases, β-TCP also known as Whitlockite); dicalcium phosphate $CaHPO_4$ (also called calcium monohydrogen phosphate, dicalcium phosphate anhydrous (DCPA) and monetite); dicalcium phosphate dihydrate (DCPD, brushite); calcium dihydrogen phosphate $Ca(H_2PO_4)_2$ (also called monocalcium phosphate); monocalcium phosphate monohydrate (MCPM); calcium pyrophosphate $Ca_2P_2O_7$ (occurs as α, β and γ phases); hydroxyapatite $Ca_{10}(PO_4)_6(OH)_2$; octocalcium phosphate $Ca_8H_2(PO_4)_6 \cdot 5H_2O$; amorphous calcium phosphate $Ca_3(PO_4)_2 \cdot nH_2O$ (ACP); precipitated hydroxyapatite $Ca_{10-x}(HPO_4)_x(PO_4)_{6-x}(OH)_{2-x}$ (PHA).

More preferably the water-consuming reactive fillers comprise a calcium-containing compound and at least one other inorganic compound, which is preferably a phosphate-containing compound, for example a further calcium phosphate compound. The water-consuming reaction may involve reaction of the component compounds with each other as well as with water. It may be an acid/base type reaction or occur due to varying solubility of different calcium phosphate species.

Preferably the water-consuming reactive filler undergoes a reaction with water which consumes at least one mole of water per mole of filler, but more preferably at least two, three, four, five or six moles, most preferably at least seven moles of water per mole of filler.

A particularly preferred filler is a mixture of β-TCP (β-$Ca_3(PO_4)_2$) which reacts with more basic MCPM ($Ca(H_2PO_4)_2 \cdot H_2O$), preferably in a 1:1 molar ratio. Without wishing to be bound by theory, it is believed that the high solubility of MCPM encourages water sorption but the fast transfer of small hydrogen ions to the less soluble β-TCP prevents its removal from the polymer into surrounding aqueous phases. This hydrogen transfer converts both reactants to a dicalcium phosphate which can then precipitate as a less soluble brushite form. (DCPD, $CaHPO_4 \cdot 2H_2O$). In this reaction 7 moles of water are consumed per mole of MCPM and β-TCP thereby reducing the effect on the absorbed water on the surrounding polymer $$\beta\text{-}Ca_3(PO_4)_2 + Ca(H_2PO_4)_2 \cdot H_2O + 7H_2O \rightarrow 4CaHPO_4 \cdot 2H_2O \quad (1)$$

The use of a 1:1 ratio ensures that the βTCP can fully react to form brushite, thereby as will be shown in the results section below can increase composite biocompatibility.

Other preferred reactive water-consuming fillers include, but are not limited to:

mixtures of tetracalcium phosphate and anhydrous dicalcium phosphate (to form hydroxyapatite);

$$2CaHPO_4 + 2Ca_4(PO_4)_2O \rightarrow Ca_{10}(PO_4)_6(OH)_2 \quad (2)$$

These components may be preferred in embodiments where the resultant composite material is to be non-degradable (for example for a tooth restoration material), particularly if fluoride is then added. This would produce fluorapatites and reduce the solubility of the hydroxyapatite further, both in the material and the surrounding tooth structure (dentine and enamel) protecting the latter from recurrant infection and caries beneath the restoration.

The dicalcium phosphate may be provided by MCPM and β-TCP and tetracalcium phosphate added to encourage further conversion to hydroxyapatite. The addition of other components other than tetracalcium phosphate is not preferred since this might encourage the formation of amorphous hydroxyapatite.

mixtures of MCPM and TCP which in the presence of calcium carbonate can form octocalcium phosphate);

$$Ca(H_2PO_4)_2 \cdot H_2O + 5Ca_3(PO_4)_2 + 9H_2O \rightarrow 2Ca_8H_2(PO_4)_6 \cdot 5H_2O \quad (3)$$

(see also refs. 42 and 43).

mixtures of β-TCP and acids such as pyrophosphoric acid or orthophosphoric acid (which would also react to form brushite);

mixtures of anhydrous calcium chloride and anhydrous sodium hydrogen phosphate (which can form brushite $CaHPO_4 \cdot 2H_2O$, or hydroxyapatite);

$$CaCl_2 + Na_2HPO_4 + 2H_2O \rightarrow CaHPO_4 \cdot 2H_2O + 2NaCl \quad (4)$$

(In this case the water soluble sodium chloride can leach out of the set polymer)

It will be appreciated that it is not necessary that all the filler in the composite is a reactive filler. For example in some embodiments (e.g. drug-releasing restorative dental composites) it may be desirable to mix reactive fillers with of the invention with conventional silica based 'glass'. This would improve strength and potentially apparence while nevertheless retaining the water-reacting and drug-releasing benefits of the fillers of the invention. However preferably at least 50, 60, 70, 80, 90, 95% of the filler is a reactive filler as described herein.

Example Polymers and Cross-Linking Compounds

In preferred embodiments of the present invention, the compound capable of (further) polymerising and/or cross-linking to form a solid polymeric matrix (the polymerisable/cross-linkable compound) may itself be a polymer. Alternatively the compound may be a monomer, which can be polymerised in situ. Some polymers, in particular short chain polymers (oligomers) may be used which are also capable of further polymerisation. The term polymer is well known in the art, and refers to a macromolecule made up of multiple repeating units (monomers). Polymers may be formed of more than one type of monomer, in which case they can also be referred to as co-polymers. Short-chain polymers of relatively low molecular weight, made up of a finite number of monomer units (for example, from 10 to 1000 units), may also be referred to as oligomers. In the context of this application, the term polymer expressly includes both short-chain (oligomers) and long-chain polymers. In some embodiments of the present invention, it is preferred that the compound is an oligomer.

Although the ensuing discussion is focussed on the use of such polymeric or oligomeric compounds, in the light of this disclosure it will be readily understood by one skilled in the art that the principles of the invention apply mutatis mutandis to the use of polymerisable monomeric compounds.

Polymers capable of cross-linking by either chemical or physical processes, which may be suitable for use in the invention, are known in the art.

Examples of polymers which may be suitable for use in this invention include, but are not limited to, polyesters (such as polylactide, polyglycolide, polycaprolactone), polyanhydrides, polyethers, polycyanoacrylates, polyvinylalcohol, polyacrylic acid, polyacrylamide, polyorthoesters, natural polymers such as hydroxybutyric acid, cellulose, chitosan, collagen and co-polymers thereof. Other non-degradable polymers include polymethylmethacrylate, polyhydroxyethylmethacrylate (HEMA), and polymers of methacrylates in dental composites such as urethane dimethacrylate (UDMA), triethylene glycol dimethacrylate (TEGDMA), BISGMA etc.

In some applications it is preferred that the polymer is degradable. The term 'degradable' refers to materials which decompose or erode over time to produce molecules, which are soluble in the surrounding medium. Preferably this degradation occurs over a timescale of a few weeks (for shorter term drug delivery devices, for example for periodontal treatment) or months (for longer term drug release and bone repair). If this decomposition occurs in biological conditions, such as inside the body, and on a biologically relevant timescale, the materials may be referred to as 'No-degradable'. Degradable polymers include poly(ether-co-esters), polyanhydrides, polyorthoesters, polycyanoacrylates and natural polymers such as polysaccharides (e.g. cellulose) or proteins (e.g. collagen).

In some applications it is preferred that the polymer is non-degradable. The term "non-degradable refers to materials which do not significantly decompose or erode over time. Depending on their application, some decomposition or erosion (for example due to mechanical wear) of the composite of the invention may be inevitable over long periods of time. Preferably, a non-degradable material does not significantly decompose or erode over a period of at least 1 year, more preferably at least 2, 3, 4, 5, 10 or 20 years.

Applications where a non-degradable polymer is preferable are described below and include restorative dentistry e.g.

tooth restoration. In this application it will be appreciated that it is acceptable that some calcium phosphate species may leach from the set material provided there is not an unacceptable decline in material strength. This leached material may remineralise the surrounding tooth structure reducing its susceptibility to recurrent caries infection. It may also fill gaps between the tooth and restoration to prevent leakage of bacterial from the surface of the tooth.

In some embodiments of the invention, it is preferred that the polymers are capable of chemical cross-linking, i.e. of forming covalent bonds between chains. Degradable polymers capable of chemical cross-linking include, but are not limited to: poly(ether-co-esters) (in particular poly(lactide-co-propylene glycol-co-lactide)) with (meth)acrylate groups on the chain ends; polyanhydrides, and polypropylene fumarates combined with other cross-linking dimethacrylates. In these preferred embodiments as well as non-degradable dental restorative materials the cross-linking generally involves acrylate or methacrylate end groups on the monomer/polymer chains. Covalent bonds may be formed by reaction of radicals generated, for example, by irradiation with UV or visible light, in the presence of an initiator and activator such as camphorquinone (CQ) and dimethylparatoluidine (DMPT) or by means of a chemical cure system that includes benzoyl peroxide (BP) with DMPT.

In certain embodiments the polymers may be capable of further polymerisation to form longer linear chains. This may be in addition to the cross-linking described above.

A mixture of different cross-linkable polymers may be used in the formulation of the invention.

Preferred cross-linkable degradable polymers for use in the formulations of the invention include short-chain poly(ether esters), polyanhydrides and polypropylene fumarates. Advantageously, these units may comprise methacrylate groups on the chain ends which enable chemical cross-linking of the chains.

Preferably the cross-linkable degradable polymers used in the present invention are short chain methacrylate capped poly(ether-co-esters). The cross-linkable polymers may have the general formula (I):

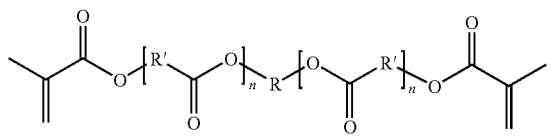

Formula (I)

wherein R' for example may be straight or branched alkyl having 1 to 10 carbon atoms, preferably $CH_2$ (glycolide), $CH(CH_3)$ (lactide) and/or $(CH_2)_5$ (caprolactone).

To increase or decrease polymer degradation rates, lactide groups may be partially replaced by caprolactone and glycolide groups, respectively. The choice of R' will therefore depend upon the specific application and the required rate of degradation. Generally, although not exclusively, with polyesters, as the ratio of carbon to oxygen atoms increases hydrophobicity is raised and degradation rate decreased and it will be appreciated that such changes may be tested and optimised without undue burden in the light of the present disclosure.

If the ester group is replaced simply by C=O, polyanhydrides are then formed upon polymerisation of the methacrylate group. In polypropylene fumarates degradable $CO_2C=CCO_2$ chemical groups are present in addition or instead of methacrylate groups. The polyesters are, however, preferable because the high reactivity of the anhydride group can make purification less easy and the sterically hindered fumarate groups can be slower to polymerise that methacrylate end groups.

R for example may be poly(propylene) glycol, poly(ethylene) glycol or poly(propylene co ethylene) glycol. With longer, more hydrophobic, chains degradation rate can be reduced. R may also be a straight chain hydrocarbon having 2 to 6 carbon atoms (derived from the corresponding terminal diols e.g. 1,2-ethanediol and 1,6-hexanediol), In principle, however, any molecule with alcohol ends may also be used to form a wide range of monomers. In dental monomers for example R is triethylene glycol (for production of TEGDMA) and Bisphenol A is used to make BISGMA. In these cases, however, the methacrylate (or acrylate) group is added directed to the alcohol end groups without the intervening degradable polyester linkage Those skilled in the art will be readily able to provide appropriate polymers for use in the invention disclosed herein without undue burden and using known methods. For example more branched polymer structures (e.g. containing 3 and 4 methacrylate groups) may be provided using glycerol $(HC(OH)(CH_2OH)_2)$, pentaerythritol $(C(CHOH)_4$ or polyvinyl alcohol in place of R.

Particularly preferable are poly(lactide-co-propylene glycol-co-lactide) dimethacrylates.

Most preferably these are triblock dimethacrylates with a central polypropylene glycol (PPG) section of molecular weight 400 to 2000 g/mol (equivalent to 7 and 34 propylene glycol units respectively), capped both ends with lactide segments (LA) with between 2 and 8 lactic acid units (equivalent to molecular weights of 144 to 576 g/mol) and then methacrylate groups. PPGnLAmDMA indicates a dimethacrylate with a total of n 'PG' and 2m 'LA' units, respectively.

These PPGnLADMA methacrylates may be formed by the method shown in FIG. 17, by ring opening polymerisation of lactides followed by the addition of methacrylate groups to either end of the chain.

Non-degradable polymers for use in the present invention are provided in similar manor to the degradable ones, except that generally the polylactide (polyester) groups will be absent. Examples of monomers commonly used in dental composites/adhesives include the monomethacrylates methylmethacrylate and HEMA and dimethacrylates, UDMA, TEGDMA and BISGMA. In other monomers acidic groups such as carboxylic or phosphoric acid are also added onto the R group to give interaction between the restorative material/adhesive and hydroxyapatite in the surrounding tooth structure. In some formulations polycarboxylic acids such as polyacrylic, polymaleic and polyitaconic or equivalent polyphosphonic acids can be added. Such acidic chemical groups could also provide greater interaction between the monomers and calcium phosphate fillers thereby raising mechanical properties. The presence of the polyacids may also aid transformation of brushite to less soluble hydroxyapatite. A wide range of such monomers and polymers are present in current dental adhesives.

In embodiments where it is preferred for cells to adhere to the composites (e.g. where they are acting as scaffolds) it may be desirable to add small amount of polymers having charged groups e.g. NH or carbon/late to the fluid compostion (e.g. approx 5-10% of the total polymers component).

Example Additives or Other Components

Preferably the filler makes up greater than 50%, 55%, 60%, 65%, 70%, 75% or 80% by weight of the formulation. In some embodiments, the formulation may preferably comprise about 60-90%, more preferably 65-85%, most preferably 75-80% filler.

The formulation may further comprise one or more of the following additives: initiators (for example photoinitiators such as camphorquinone with NN-dimethyl-p-toluidine (DMPT) or 2-(N,N-dimethylamino)ethyl methacrylate (DMAEMA), benzoin, Irgacure 651®, phenylpropanedione (PPD), monoacylphosphate oxide (Lucirin TPO), bisacylphosphine oxide (Irgacure 819), benzyldimethyl ketal (Igracure 651, chemical initiators such as benzoyl peroxide with DMPT) (preferably at concentrations between 0.25 and 2 wt % of the fluid phase), diluent monomers to improve monomer fluidity and initiator dispersion (at 2 to 20 wt % of the fluid phase)(such as hydroxyethylmethacrylate (HEMA), triethylene glycol dimethacrylate (TEGDMA), and other mono or multifunctional (meth)acrylates. The multifunctional methacrylates may additionally raise crosslinking and reduce water sorption. Other additives may include hydroxyquinone to act as a stabiliser (preferably at 0.005 to 0.05 wt %).

Generally speaking, because the fillers of the invention themselves absorb water, HEMA is not required to provide hydrophilicity (which property assists release of actives as described below).

The formulation of the invention may optionally also comprise an active agent such as a pharmaceutical or biological molecule for delivery to a site of use. Examples of active agents include antibiotics (eg gentamicin, tetracycline, oxycycline, minocycline), other antibacterial and antifungal agents (chlorhexidine, cetyl pyridinium chloride, thymol), anti-inflammatory agents (prednisolone and ketoprofen), analgesics (morphine, codeine), Preferably these active agents are present in the formulation in quantities between 1 and 20 wt %. Additionally other bone-repair agents, DNA, and proteins (particularly bone morphogenic proteins) at lower levels (0.01 to 1 wt %) can be included.

As described below, other ions such as fluoride, hydroxide, acid or buffers may be added to the aqueous phase if present.

Proteins to encourage selective cell adhesion may be added (e.g. directly into the formulations, or adsorbed onto the surface of preformed composite implants).

Composite Materials

Another aspect of the present invention provides a composite material, comprising a polymer matrix and a water consuming reactive filler distributed in said matrix. Said filler is capable of reaction with water absorbed into the polymer matrix to produce a solid material, wherein said solid material is better dispersed throughout the polymer matrix than the unreacted filler.

Preferably this composite material is formed from a fluid formulation according to the invention. Polymerisation/cross-linking of the compound therein produces the polymer matrix, incorporating the particles of the filler within said matrix. These particles may preferably be in the range of 0.5 to 200 µm in size. Preferably the composite is formed by cross-linking of a preferred fluid formulation as described above, wherein the polymerisable/cross-linkable compound is a polymer or oligomer.

As described above, such composites may be used, for example, as fillers, scaffolds, or membranes in bone or other tissue repair, cements or adhesives in fixing bio-implants, restorative dental or other medical composites per se, or to release or provide actives such as bacteriocides (either in these contexts, or as preparations solely for that purpose).

A still further aspect of the present invention provides a hydrated composite material, comprising a polymer matrix and a solid material dispersed throughout said polymer matrix. Said solid material may be produced from a water-consuming reactive filler, by reaction of said water-consuming reactive filler with water absorbed into the polymer matrix.

Preferably the hydrated composite material may be formed from the previously described composite material of the invention, by reaction of the water-consuming reactive filler with water absorbed by the polymer matrix. Preferably the solid material produced from this reaction is well dispersed through the polymer matrix, preferably filling both the regions previously occupied by the original particles but in addition more homogeneously interdispersed (on the 10 to 100 nm scale range) within the polymer phase.

A composite material is a complex material, in which two or more distinct, structurally complementary substances, especially glasses or polymers, combine to produce structural or functional properties which differ from those of any individual component.

In the context of this application, the term 'composite material' refers to a material formed from setting or curing of a fluid formulation, such as a formulation according to the invention, comprising a polymer matrix, preferably a cross-linked polymer matrix, and dispersed solid particles. In different embodiments, the solid particles may be made up of the water-consuming reactive filler described above, of the material produced when said filler has reacted with water, or of a mixture comprising these species. Preferably, the reactive filler is at least 50%, 60%, 70%, more preferably at least 80% reacted in the hydrated composite material. This may be confirmed by use if the tests and techniques described herein. Preferred reactive filler species, and the materials formed therefrom, are discussed above.

As described above for the fluid formulations, the formation of the polymer matrix may be by either chemical or physical mechanisms, including cross-linking. Preferred cross-linkable polymers, from which the polymer matrix may be formed, are discussed above.

Preferably, the solid particles of the composite are initially well distributed throughout the polymer matrix. As described above, reaction of the water-consuming reactive filler particles with water absorbed by the polymer matrix results in the production of a more homogeneous structure (see FIGS. 5 and 12).

Raising homogeneity via reaction of the filler particles is potentially advantageous for many reasons, primarily because the weak abrupt interfacial region between the polymer and filler is lost. This may improve mechanical and wear characteristics. The inorganic and polymer phases are also more likely to dissolve/degrade together if the organic and inorganic phases are interacting at the molecular level rather than purely at polymer particle interfaces. Addition of filler can also provide a means to alter the rate of polymer degradation (in embodiments wherein the polymer is degradable). Further, its simultaneous release with any acidic degradation products (which are produced during degradation of many biomedical degradable polymers) may buffer the surroundings and reduce any acid irritant effects. Such buffers may also prevent bulk catastrophic degradation of polymers which can occur with build up of acidic products in the material cores.

Examples of mechanical properties which may be improved include surface hardness, elasticity, dynamic modulus, compressive and flexural strength and wear resistance. Other properties which may be improved in the composites of the invention, compared to polymerised/cross-linked compounds in the absence of fillers, include cell compatibility/attachment, a reduction in the heat or shrinkage generated during polymerisation/cross-linking, due to the lower volume fraction of the polymer, and degradation, which may be easier to control through variations in filler loading.

Advantageously, the properties of the composite may be controlled by altering the properties of the polymerisable/cross-linkable compound. For example, in some embodiments, reducing the chain length of the polymer in the fluid formulation of the invention, significantly raises the initial modulus of the cross-linked polymers themselves (as shown in FIG. 7), providing a higher starting point, which the addition of filler would raise further. Reducing the polymer chain flexibility through addition of bulky side chains or using diol endcapped alkanes (eg 1,2 ethanediol, or 1,6 hexandiol etc) or other multifunctional alcohols (including pentaerithritol ($C(CH_2OH)_4$), glycerol ($HC(OH)(CH_2OH)_2$), polyvinyl alcohol etc.) instead of the polyether PPG would also raise the initial polymer modulus. Other variables, such as the amount and identity of the filler, may also affect the final mechanical properties of the composite.

As will be appreciated by those in the art, the choice of preferred filler may vary depending on the type of polymerisable/cross-linkable compound used, and vice versa. Depending on the required properties for a particular composite, different combinations of the preferences laid out above may be suitable. The optimum choice and amount of filler may also be dependent on the degree of cross-linking of the polymer, for example. Increasing cross-linking, for example by reducing the length of polymer chains in the initial formulation, may reduce the amount of water sorption.

Control of mechanical properties is particularly useful in the development of materials for use in bone repair applications, where properties close to those of real bone are optimal (Refs 36-39).

It is preferable that the strength of the material (the stress at which the material breaks) is as high as possible so that it may be used in both weight-bearing bone fixation (eg in the lower body) and in filling of regions where stresses may be minimal. Bone strengths are dependent upon age and health of a subject as well as type (cortical versus cancellous) and location but can be over 150 MPa in both compression and tension.

In addition the modulus of a bone-fixation material and its response to any forces should preferably be comparable to that of the surrounding tissue. For elastic solids modulus may be defined as stress divided by strain. Stress is the force per unit area and strain the extension per unit length. Calcium phosphate cements are generally brittle with high modulus and a low level of strain at break point but polymers can be much more flexible and extend much further before break. Polymers are also viscoelastic in that modulus can vary with time and flow can occur under a continuous stress as occurs with a liquid. This viscoelastic mechanical behaviour can be monitored using dynamic mechanical analysis which provides both the storage modulus (which can be identified with the elastic nature of the material) and the loss modulus (which quantifies the fluid nature of the polymer). Bone, being a composite of collagen and hydroxyapatite, has an intermediate modulus whose viscoelastic behaviour is more likely to be matched using a combination of calcium phosphate and polymer rather than either individually. The modulus of bone, or of any material, is dependant upon the exact mode of measurement, which can vary widely. Bone typically has an elastic or storage modulus of the order of 10 GPa.

In preferred embodiments of the present invention, the mechanical properties of the composite material are closer to those of real bone, than those of the polymerised/cross-linked compound in the absence of filler. More preferably, the mechanical properties of the composites after reaction of the fillers with the absorbed water are closer to those of bone than before this reaction occurs. In more preferred embodiments, the mechanical properties of the composites, at least in the early stages of material placement (i.e. within a few hours after injecting and setting/curing) are a close match to those of bone.

Mechanical properties of bone (see Refs 25-28) may include, but are not limited to:

Elastic modulus (E):
  Low strain ~10-20 GPa
  High strain ~10 GPa
Dynamic modulus
  Storage E' ~8 GPa
  Loss E" ~0.2 GPa
Strength
  Compressive 5-10 MPa (cancellous) 130-220 MPa (cortical)
  Tensile 5-10 MPa (cancellous) 80-150 MPa (cortical)

In some embodiments it may be preferable that the composites of the invention are degradable. More preferably this degradation occurs from the surface of the composite, in a controlled manner. Preferably the inorganic particles and the polymeric matrix degrade at approximately the same rate. This may in preferred embodiments be readily controllable over periods ranging from days to months for different applications. For periodontal treatment, for example, the material should degrade in about 6 weeks but for large bone defects the material would need to remain in place for much longer but preferably become porous and permeable to cells with time, so as to act as a scaffold for new bone formation. If the degradation products of the polymer are acidic (for example, polylactides degrade to release lactic acid) it is preferred that the degradation products of the inorganic particles are basic, and create a buffering effect to neutralise these acidic products.

In other embodiments it may be preferable that the composites of the invention are non-degradable. The term "non-degradable" refers to materials which do not significantly decompose or erode over time. Some decomposition or erosion (for example due to mechanical wear) may be inevitable over long periods of time. Preferably, a non-degradable material does not significantly decompose or erode over a period of at least 1 year, more preferably at least 2, 3, 4, 5, 10 or 20 years.

Applications where a non-degradable composite is preferable include restorative dentistry e.g. tooth restoration Processes A further aspect of the present invention provides a process for production of a composite material comprising the steps of:
i) providing a fluid formulation comprising at least one compound capable of polymerisation and/or cross-linking and a water-consuming reactive filler;
ii) optionally injecting said formulation into a site of use;
iii) polymerising and/or cross-linking said compound, to form a solid polymer matrix;
iv) causing or allowing said filler to react with water absorbed by said polymer matrix, to produce a solid material which is dispersed throughout the polymer matrix.

Said solid material may have a density lower than that of said water-consuming reactive filler. This can be advantageous if swelling of the material occurs sufficient to counteract polymerisation shrinkage.

Preferably the formulation provided in step (i) of the process of the invention is a fluid formulation according to the invention, and the process results in a composite material according to the invention, as described in detail above. The preferences and embodiments described above, in the context of said formulations and said composite materials, apply mutatis mutandis to the process of the invention.

Preferably the polymerisation/cross-linking step (iii) occurs rapidly, with reaction at least 70%, 75%, 80%, 85%, more preferably at least 90%, complete within 24 hours. The polymerisation/cross-linking may be performed by the use of light, most preferably a blue dental light, LED, or laser, and setting to form the polymer matrix occurs with short exposure times (preferably less than 1 minute). In other preferred embodiments, the polymerisation/cross-linking may be due to the presence of chemical initiators. In embodiments where the cross-linking is physical cross-linking, for example polymer crystallisation, it may preferably be performed by removal of excess solvent, for example by evaporation, or compression moulding.

Preferably the reaction in step (iv) occurs spontaneously upon absorption of water by the polymer.

Other Methods and Utilities of the Present Invention

Still further aspects of the present invention provide uses of the formulations and composites of the invention, for example in bio-medical applications.

The formulations of the invention are capable of being injected into a site of use. Curing or setting may then be performed in situ to form a solid polymeric matrix, which will be micro-mechanically adhered to the surrounding tissue. Absorption of water into the polymer matrix will then cause dissolution, reaction and re-precipitation of the fillers, as described in detail above, thus improving the properties of the composite material.

The composites of the invention may therefore be useful in bone repair applications, particularly when calcium phosphate fillers are used since the composite will release calcium and phosphate ions as it degrades, which are needed for the inorganic component of bone, hydroxyapatite. With simultaneous slow release of calcium and phosphate with the remainder of the device these components will provide continual release of the ions required for the surrounding bone to reform at the same rate at which the device erodes. The ionic products from the degradation of the fillers also serve to buffer any acidic degradation products from the polymeric components of the composites—this prevents local irritation caused by acid build up.

A fluid adhesive formulation may be injected onto the fracture site before realignment to then help keep the fractured bone in place during the early stages of repair but finally degrade to allow complete repair. More viscous formulations can be used as fillers with large defects in bones that may be present, for example after removal of a tumour. In this case it may be preferable for the formulations to develop porosity through, for example, release of soluble phosphate glasses within a few days, so that the material can act as a scaffold for new bone formation.

A further aspect of the present invention therefore provides a method of wound healing or bone repair comprising the steps of:
i) providing a fluid formulation according to the invention;
ii) injecting said formulation into the site of bone damage;
iii) curing said formulation to form a composite material according to the invention, wherein said composite is adhered to the damaged bone;
iv) causing or allowing the filler in said formulation to react with water absorbed by said polymer matrix to produce a solid material, wherein said solid material is better dispersed throughout the polymer matrix;
v) allowing degradation of said composite material, and concomitant growth of new bone tissue.

A still further aspect of the present invention provides the use of a formulation of the invention in wound healing or bone repair (or in the preparation of medicament, carrier, or implant for these things) for example as described above.

The polymeric composites of the invention are also suitable for use as drug or DNA delivery devices, if these active compounds are incorporated into the formulations.

The composites of the invention may additionally be used as cements or adhesives for fixation of implants, such as in dental or maxillofacial surgery. For example titanium implants in dental applications may require a fixative, if there is not enough bone present to initially support the implant. The composites of the invention may be used to initially fix the implant in place but upon degradation create an area for new bone to grow and permanently anchor it. In this case development of porosity for example through leaching of the more soluble phosphate glasses can provide a scaffold into which cells could grow. To ensure channels to the pores formed by phosphate particles are generated soluble phosphate fibres could be used as well as particles.

Accordingly, an aspect of the present invention provides a method for fixation of a dental or surgical implant into a cavity or location, comprising the steps of:
i) providing a fluid formulation according to the invention;
ii) injecting said formulation into the cavity or location;
iii) curing said formulation to produce a composite material according to the invention, said composite material adhering to said dental or surgical implant;
iv) causing or allowing the filler in said formulation to react with water absorbed by said polymer matrix to produce a solid material, wherein said solid material is better dispersed throughout the polymer matrix.

A further aspect of the present invention provides the use of a formulation according to the invention for fixing a dental or surgical implant (or in the preparation of medicament, carrier, or implant for these) for example as described above The composites of the invention may additionally be used as restorative composites or adhesives. These may be used, for example, in restorative dentistry. Preferably these composites are non-degradable and active-releasing. They should preferably additionally swell upon water sorption just sufficiently (approximately 3 to 10 volume % dependant upon the volume, molecular weight and level of polymerisation of the methacrylate monomers) to compensate for polymerisation shrinkage in order to reduce bacterial microleakage.

One benefit of the composites of the invention in this aspect is that calcium phosphates from the fillers may bind to the surrounding hydroxyapatite in tooth structure thereby improving adhesion. Water sorption induced swelling should also reduce gaps generated by polymerisation shrinkage between the tooth and restoration to below the size (typically less than 1 micron) through which bacteria could penetrate. Water could additionally encourage diffusion controlled release of antibacterial agents before it becomes bound by the calcium phosphate fillers. Reprecipitation of the fillers within the polymer structure should additionally enable holes left upon release of drug to be filled.

Accordingly, an aspect of the present invention provides a method for providing a dental composite or implant at cavity or location, comprising the steps of:
i) providing a fluid formulation according to the invention;
ii) injecting said formulation into the suitably prepared cavity or location;
iii) curing said formulation to produce a non-degradable composite material according to the invention
iv) causing or allowing the filler in said formulation to react with water absorbed by said polymer matrix to produce a solid material, wherein said solid material is better dispersed throughout the polymer matrix.

v) optionally release of active agents (particularly antibacterial agents) from the formulation in the invention may additionally occur through diffusion Step (iii) may be followed by addition, on top of the composite, of a further direct or indirect composite restoration. The formulation may additionally be cured in layers by methods commonly employed by dentists to reduce detrimental effects of polymerisation shrinkage.

Thus a further aspect of the present invention provides the composites of the invention (especially non-degradable ones) for use as a dental composite/adhesive. In some embodiments the composites may be used as an adhesive (liner) for stronger indirect composite tooth restorations, or underneath a stronger direct injectable composite material (sandwiching technique). The invention may additionally itself be used to prepare an indirect restoration (i.e. a restoration that is precured and then glued in place possibly with some of the uncured invention or other dental composite adhesive). The new composite invention could also be used as a liner/adhesive for amalgam restorations or for fixing of posts or other metal devices used in dentistry (eg. Orthodontic braces and gold restorations). In some embodiments it may be particularly desirable to use a chemical cure (e.g. benzoyl peroxide and DMPT) instead of camphor quinine initiated light cure as described above or a combination of light and chemical cure. Chemical cure would be particularly useful if a restoration is deep or the invention is used beneath a non light transparent material.

Preferably such composites further comprise an active agent e.g. chlorhexidine. Optionally the composites in this aspect will use a mixture of reactive fillers and conventional (e.g. Silica based) fillers.

Accordingly, an aspect of the present invention provides a method of delivery of an active agent, comprising the steps of:
  i) providing a fluid formulation according to the invention, wherein said formulation comprises an active agent;
  ii) injecting said formulation into a site of use;
  iii) curing said formulation to produce a composite material according to the invention;
  iv) causing or allowing the filler in said formulation to react with water absorbed by said polymer matrix to produce a solid material, wherein said solid material is better dispersed throughout the polymer matrix;
  v) allowing a) degradation of said composite material with concomitant release of said active agent or b) water sorption to encourage diffusion controlled drug release.

A further aspect of the invention provides the use of a formulation according to the invention in a method of delivery of an active agent (or in the preparation of medicament, carrier, or implant for this) for example as described above. One potential advantage of having water sorption encourage diffusion controlled release is that as the material swells drug diffusion rate through the polymer/composite can increase. The can lead to drug release rate being more linear with time than generally obtained with diffusion controlled drug release from polymers. Such linear release of drugs can also be gained if it is controlled primarily by surface erosion of the composite material or release is controlled by a combination of diffusion and surrounding material degradation.

Examples of active agents which may be suitable for use in the invention have been previously discussed in relation to the formulations of the invention.

For example, in the treatment of periodontal disease which is caused by bacteria, polymeric materials impregnated with anti-bacterial drugs are commonly implanted into the periodontal cavity to provide an in situ release of the drugs. These implants (for example, commercial products such as PerioChip® or Actisite®) tend to release the antibacterial agents very quickly, and can move about within the cavity and become dislodged. The formulations of the present invention can be injected into the periodontal cavity, and upon curing would be fixed in place. The injectability allows the material to penetrate deeper into a pocket than would be possible with a solid device and thus it may be applied more easily. Additionally, the injectability of the formulations of the present invention may enable them to adhere more strongly. Slow, controlled degradation would then provide a slower, more controlled release of drugs to the affected area.

As shown in the Examples below, composites of the present invention can demonstrate twice the levels of drug or other active release compared with the polymers alone. Without wishing to be bound by theory, it is believed that this may be due to the inclusion of the reactive fillers, possibly because they encourage water sorption or the formation of channels in the material structure.

As noted above in certain embodiments, for example wherein the fluid formulations are to be using in restorative dentistry, antibiotic, antibacterial or antifungal agents may be particularly preferred. The most significant risk in restorative dentistry is leakage of bacteria between the tooth and restoration (bacterial microleakage).

It is known in the art to try and prevent this problem using fluoride release. For example, in the dental field polyacids have been added to composite restorative materials to produce compomers. These encourage some limited water sorption and reaction between the polyacid and basic glass filler particles to promote fluoride release. The level of this reaction in such compomers, contrary to the following new invention, however, is primarily only at the surface of the materials and filler particles. Fluoride release from the glasses in such compomers is additionally limited and not sufficient for effective antibacterial action which had been the original hope with such materials. Current high fluoride releasing formulations have low strength.

Chlorhexidine is considered the gold standard antibacterial agent (non antibiotic) for the oral cavity. It has to date, however, been difficult to get chlorhexidine to be released from dental restorative materials. This problem may be addressed by use of the reactive fillers in the degradable and non degradable composites of the present invention. The chlorhexidine levels released by non degradable composites of the present invention have been shown to be effective against bacteria on agar (unlike fluoride releasing materials) and in a broth.

Another use of the composites of the invention in periodontal disease is in Guided Tissue Regeneration (GTR). During GTR therapy (for teeth), the soft gum tissue is surgically separated from the endangered tooth and the tooth surface is thoroughly cleaned and infected tissues are removed from the area. After cleaning a small piece of material called a GTR membrane is placed against the tooth. This GTR membrane serves as a barrier that separates fast-growing soft (gum) tissue and bacteria from the newly cleaned surface of the tooth root where bone and the periodontal ligament need to reform. The membrane enables slower-growing fibers and bone cells to migrate into the protected void area but should also be permeable to fluid and proteins but not bacteria. Newer GTR membranes produced from the polyester polyglycolide are degradable but not drug releasing. As mentioned above, however, bulk catastrophic degradation of polyesters can be a problem in biomedical applications. In addition poor control over degradation with healing can also lead to the GTR membrane being forced out and visible above the gum line. They must additionally be fixed in place with sutures which requires significant dexterity, skill and experience. Use of the new materials as a combination of a membrane and adhesive both containing calcium phosphates and antibacterial agents may provide a wide range of new materials that would be easier to use and may be much better suited than simple polyesters. It may be possible, for example, to control the membrane structure so that the lowest part of the membrane degrades faster as the bone grows up, preventing it from being forced from the pocket before the whole material has time to degrade. Slow release of antibacterial agents during the repair would reduce the possibility of re-infection. Calcium and phosphate release would provide the ions required for bone repair and other components may be added to enhance the rate of bone regrowth.

In these periodontal applications the modulus and strength of the material do not need to be as high as for bone repair, as the device is adjacent to soft tissue and will not be load-bearing.

A particularly preferred use of the formulations and composites of the invention is in delivery devices for large delicate molecules, such as polymers, proteins (particularly bone polymorphic proteins) or nucleic acids, such as DNA. Advantageously, curing of the formulations of the invention may be accomplished by many different means, as discussed previously, and the type of polymerisable/cross-linkable compound used in the formulation can therefore be tailored to the requirements of the drug to be released. For example UV-sensitive molecules will not be affected if a blue LED light, or alternatively a chemical curing agent, is used for curing.

The composites of the invention, in particular those comprising calcium phosphate compounds, are particularly suited to DNA delivery.

The development of effective and safe protocols for the delivery of genes to alleviate a wide range of genetic abnormalities is of major importance. One attractive alternative to conventional viral and particulate systems is the co-precipitation of genes with calcium phosphate. Although such precipitation has been used with some success for gene transfer in vitro for many years, its application in gene therapy has been limited by a number of problems including 1) inability to protect the gene from degradative enzymes 2) the sensitivity of precipitate structure/chemistry to small changes in pH or the presence of other components (see Yang and Yang, Biomaterials, 18, 213-217 (1997) and 3) difficulties with in vivo targeting. Such parameters significantly affect cellular uptake and stability within the cell and thus the overall functional efficiency of transferred genes.

Recently, however, gene-containing calcium phosphate nanoparticles (<100 nm) have been produced using reverse microemulsions. These nanoparticles gave comparable in vitro transfection efficiency to the commercial agent Superfect and also demonstrated some in vivo gene expression (see Bisht et al., International Journal of Pharmaceutics, 288, 157-168 (2005); Roy et al., International Journal of Pharmaceutics, 250, 25-33 (2003). Significantly, the entrapped gene was protected from degradative enzymes, probably because the water soluble DNA remains near the centre of the microemulson droplet whilst the insoluble calcium phosphate forms a protecting shell at the oil/water interface.

One benefit of non-viral delivery is that DNA integration into the chromosome can be prevented. A disadvantage, however, is that repeated administration is then required.

For this reason a number of authors have attempted to produce slow DNA-releasing polymers. An ideal DNA delivery device should be biocompatible and initially fluid, but then able to set rapidly at the site of the target tissue to provide a slow release reserviour. It should then degrade enabling continuous controlled availability of the gene to cells near the material surface. A large number of sustained DNA delivery devices have thus far been produced, including lactide co glycolide scaffolds (Jang and Shea, Journal of Controlled Release, 86, 157-168 (2003)) and photo-crosslinked polyanhydrides (Quick et al., Journal of Controlled Release, 97, 333-343 (2004)) and poly(ethylene glycol co lactide) hydrogels (Quick and Anseth, Journal of Controlled Release, 96, 341-351 (2004)). Problems with these preparations as sustained release formulations, however, include DNA damage due either to production of free radicals during set and/or acid during degradation or non linear degradation and concomitant burst DNA rather than constant release. If, however, DNA were to be incorporated within the composites of the present invention then many of these problems could be overcome.

Specifically, in this application the DNA may for example be incorporated within water droplets dispersed within the polymer composites. As the fillers dissolve and re-precipitate around the water droplets, the DNA will be condensed within giving PolyGeneCaP formulations. The structure of the DNA/calcium phosphate is expected to be similar to the DNA-containing nanoparticles formed previously using microemulsions. Within such structures the DNA can be protected from both enzymes and acid. This provides a means to protect the DNA from acid as the polymer degrades. The DNA may then additionally be released with the calcium phosphate in a condensed form that may more readily pass through the membrane of cells. Provided the DNA remains inside calcium phosphate nanoparticles whilst traversing across the cell it can additionally be protected from enzymes and acid of the lysosomes. Through slow degradation of the degradable composites of the present invention sustained release of DNA within calcium phosphate nanoparticles will be possible.

Accordingly a preferred aspect of the present invention provides a method of DNA delivery comprising the steps of:
i) providing a formulation according to the invention, containing in addition the desired DNA molecules;
ii) injecting said formulation into a treatment site;
iii) curing said formulation to produce a composite material according to the invention;
iv) causing or allowing the filler in said formulation to react with water absorbed by said polymer matrix to produce a solid material, wherein said solid material is better dispersed throughout the polymer matrix
v) allowing degradation of said composite material with concomitant release of DNA molecules.

The DNA molecules released in step (v) may preferably be protected within calcium and phosphate nanoparticles. The method of DNA delivery may be employed in the treatment of many genetic disorders (such as lysozomal storage disorders) of which Mucopolysaccharidosis (MPS) type VII (Sly disease) is a good model for testing new formulations.

A further aspect of the invention provides the use of a formulation according to the invention in a method of DNA delivery (or in the preparation of medicament, carrier, or implant for this) for example as described above.

Thus the invention provides for the production of such DNA-containing calcium phosphate nanoparticles within a microemulsion. The microemulsion based on the compositions of the present invention includes aqueous DNA. This can be injected into the body and rapidly set. The source of calcium phosphate is a reactive filler of the present invention. The fluid formulation could also be injected and set in the body using LED lights and fibre optic technology. Since light curing is only suitable for thin specimens and in limited clinical situations it may be preferable to use chemical initiators for curing as described above.

Preferred polymers for use in the composites of this aspect employ dimethacrylate monomers, more preferably poly(lactide-co-propylene glycol-co-lactide) dimethacrylates having Formula (I) defined above, as the substitute oil phase. In addition poly(propylene-co-ethylene glycol) surfactants may be required as an emulsion stabiliser. The dimethacrylates can polymerise rapidly with less than 60 s exposure to a dental light cure gun and then with careful control over exact structure be made to degrade from the surface, linearly with time (Ho and Young, European Polymer Journal, 42, 1775-1785 (2006).

In the present invention, the addition of other ions (eg fluoride) may be used to control phosphate solubility.

The slow-release of DNA, as can be attained using formulations of the present invention are therefore of great benefit in providing prolonged treatment as well as a constant supply of the DNA in the body to increase the chance of successful and continuing uptake.

As well as applications where the formulations are injected directly into a site of use, the composites of the present invention may also be used in a pre-cured form. For example, in the GTR method discussed above or with stereolithography techniques, such as for the production of implants to replace missing parts of the body e.g. jawbone. Medical imaging techniques such as nuclear magnetic resonance (NMR), can be used to provide a computer image of missing or damaged parts of the skeleton and surrounding soft tissue. A stereolithography set-up then uses a computer-controlled laser to cure the polymeric formulation, layer by layer, to create the 3D implant corresponding to the missing part [1-3]. The material can be produced using different composites and polymers for the hard and soft tissue and may also be made porous, providing a framework for new bone cell growth.

The formulations of the present invention, having the properties of mouldability/injectability and rapid setting are particularly suitable for use in this technique. Additionally, drug molecules can be incorporated into the formulations, as discussed above, and the resultant implants would then benefit from controlled drug release as the composite degrades. Additionally the composites can be used in fluid injectable form to bond the pre-formed implant in place.

Therefore a further aspect of the present invention provides the use of formulations and composites according to the invention in stereolithography techniques. In particularly preferred aspects, formulations and composites according to the invention are provided for use in stereolithography techniques for the production of dental or surgical implants.

Kits

A further aspect of the present invention provides a kit for producing a fluid formulation and/or a composite material according to the invention, comprising:
- at least one compound capable of polymerising and/or cross-linking to form a solid polymer matrix;
- a water-consuming reactive filler, capable of reaction with water absorbed into the polymer matrix to produce a solid material, wherein said solid material is better dispersed throughout the polymer matrix;
- optionally an active agent for delivery; and
- optionally written instructions for combining said compound and said filler and curing them.

Preferably the polymerisable/cross-linkable compound and the water-consuming reactive filler are as described above.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

EXAMPLES

Summary of Examples 1 to 5

The mechanical properties of example composites of the invention, including reactive fillers, have been compared by the present inventors to a) composites with phosphate glass fillers, and b) set polymer with no filler.

As described in more detail below, upon water sorption by the reactive filler composite, values for loss and storage moduli increase over 24 hours, to around 10 times higher than the polymer alone. With phosphate glass fillers, the modulus remains low at all times.

It has also been shown that, once the initial expansion of the composite has occurred, the surface hardness of the composite of the invention remains stable despite further increase in water content and significant degradation of the composite. In contrast, although initial surface hardness is increased by addition of the phosphate glass fillers, this effect is short-lived and, upon continued water sorption, the hardness of these composites is less than that of the polymer alone. Expansion of the phosphate glass composites, followed by rapid filler release causes significant variations in the surface hardness, whereas with the reactive filler composites the hardness remains stable.

A further property which was shown to be greatly improved in the composites of the invention is the dimensional stability of the composites. Composites containing the phosphate glass fillers expand too much to be useful in bone repair applications. The composite of the invention, although initially expanding more than the polymer alone, is then dimensionally stable. Some expansion may be beneficial as it counteracts polymerisation shrinkage of the monomer (typically 5-10% by volume). With the composite of the invention, the water-induced expansion is better controlled.

Figure 17:
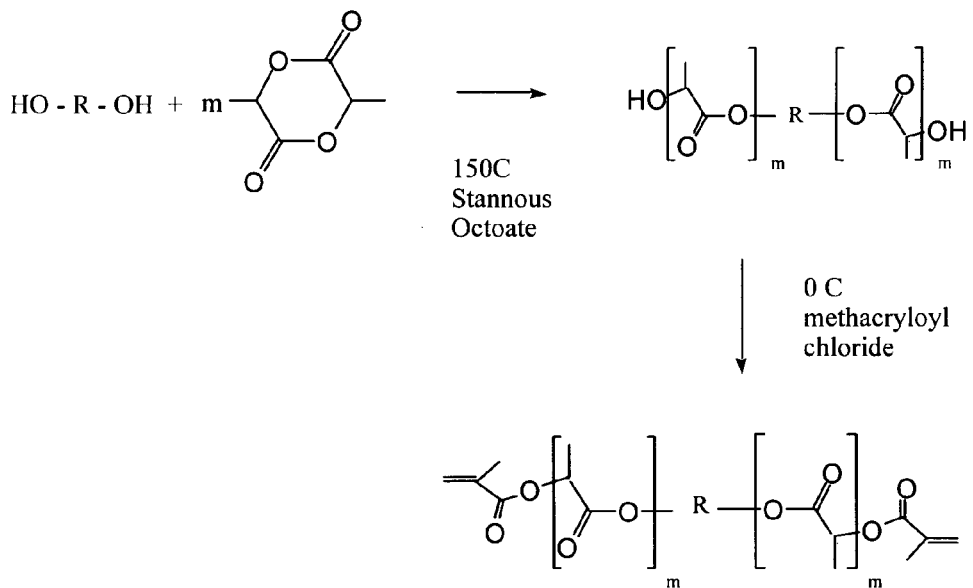
FIG. 17: Example method by which a range of biodegradable di methacrylate lactide monomers can be produced.

Additionally, via Raman spectroscopy it has been shown that the phosphates and polymer in the composite become better mixed after water sorption and reaction of the filler.
Materials and Methods Unless otherwise stated the degradable polymer is produced using poly(lactide-co-propylene glycol-co-lactide) dimethacrylate prepared as in FIG. 17 with PPG of molecular weight 1000 g/mol and PPG:lactide molar ratio of 1:4 (termed P17L4). Powder liquid ratio of degradable composites obtained using this monomer is 2:1 by weight. Non-degradable reactive filler formulations contain as the monomer phase HEMA:UDMA:TEGDMA in the ratio 2:1:1. Initiator levels are generally 1 wt % CQ and DMPT relative to the monomer phase and all formulations set using blue light exposure.

Polymerisation kinetics of the monomers was generally determined using a combination of FTIR and Raman spectroscopy. Attenuated Total Reflectance Fourier Transform Infra-Red (ATR-FTIR) and conventional Raman spectroscopy were performed using a Perkin Elmer series 2000 FTIR/Raman spectrometer, with a Golden Gate™ diamond ATR FTIR top-plate where needed. Temperature was maintained using a RS232 Specac 3000 Series™ temperature controller. Timed FT-IR spectra were obtained using Timebase software (Perkin Elmer).

The structure of the degradable monomers was confirmed using $^1$H-Nuclear Magnetic Resonance (NMR) with a Varian Unity plus 500 MHz instrument, using deuterated chloroform solvent.

Mass and volume changes of set composite materials were determined via gravimetric analysis using a Mettler Toledo density kit.

pH of the storage solutions and thereby acid release was measured using a pH meter (Hanna Instruments, pH 211).

For analysis of anion release (phosphates and polyphosphates), a Dionex ICS-2500 system consisting of a 25-μl sample loop was used, equipped with an Ion Pac® AS16 separator column and an ASRS® self-regenerating suppressor, using deionised water as the mobile phase at a flow rate of 1.5 ml/min. Data analysis was performed using the Chromeleon® software package. Calibration was obtained with standard solutions containing 1, 10, 25 and 50 ppm of sodium phosphate tribasic ($Na_3PO_4$), trisodium trimetaphosphate ($Na_3P_3O_9$), pentasodium tripolyphosphate ($Na_5P_3O_{10}$) (all from Sigma) and tetrasodium pyrophosphate ($Na_4P_2O_7$) (BDH). Results were converted from ppm of the phosphate species to mM of phosphorous atom per specimen.

For the analysis of sodium ($Na^+$) and calcium ($Ca^{2+}$) release a Dionex ICS-1000 system equipped with an Ion Pac® CS12A separator column and a CAES® electrolytic suppressor was used, with a mobile phase of aqueous 30 mM methylsulphonic acid at a flow rate of 1 ml/min. An injection loop of 25 μl with an AS50 autosampler was used. All samples were pretreated with a Dionex Onguard® IIA cartridge to remove bound phosphates and polymers. Calibration was obtained with standard solutions containing 1, 10, 25 and 50 ppm of sodium chloride (Sigma) and calcium chloride (BDH) but final data was converted to mM specimen$^{-1}$ to enable comparison with other ion release results.

Dynamic mechanical properties were tested on a Perkin Elmer Dynamic Mechanical Analyser (DMA 7e, Perkin Elmer Instruments).

Surface Raman mapping studies were carried out using a LabRAM 300 mapping spectrometer (Horiba Yobin Yvon) with a 633 nm laser, over a wavenumber range of 500 to 1500 cm$^{-1}$, step size of 4 μm and area of 300 by 100 μm.

Further Raman mapping was performed using a LabRam spectrometer (Horiba Jobin Yvon) with a 633 nm laser, ×50 objective and 1800 grating over a wavenumber range of 700 to 1600 cm$^{-1}$. Prior to analysis, the top approximately 300 micron layer of the sample was removed with a razor to gain spectra and images representative of the sample bulk. Areas 200 by 200 micron square were analysed using a step size of 5 micron. The average spectra and those at individual points were compared with raman spectra of MCPM, β-TCP, P17L4 polymer and brushite cement (formed by reacting MCPM and β-TCP with water). To generate maps of chemical homogeneity/structure, modeling software with the LabRam was used.

Scanning electron microscopy (SEM) images and energy dispersive X-ray (EDAX) analysis were obtained for the composite F4 when dry and after submersion in water for 2 weeks. The specimen was split into slices longitudinally. The cut specimen was fixed in 3% (v/v) gluteraldehyde at 4° C. overnight, then dehydrated with alcohol, followed by coating with gold and palladium (Polaron E5000 sputter coater) prior to examination of the cut surface with SEM (Cambridge 90B, Leica) equipped with EDAX analysis (Inca 300, Oxford Instruments Analytical). Five SEM images of different areas on the specimen cut surface were taken, within each image 32 EDAX spectra were obtained producing in total of 160 points of EDAX analysis. At each point the ratio of the elements calcium to phosphorus (Ca/P) was calculated, and mean, standard deviation and 95% confidence interval (i.e. $2*s/\sqrt{n}$) obtained.

X-ray diffraction (XRD) patterns, were obtained for the composite F4 when dry and after 24 hours in water. The ground specimen was placed in an X-ray diffractometer (Philips PW1780), and the data was collected using Cu $K_\alpha$ radiation. Data was collected from 10° to 40° 2θ with a step size of 0.02° and a count time of 12 seconds. The crystallised phases were identified using the Crystallographica Search-Match software (Oxford Cryosystems, Oxford, UK) and the International Centre for Diffraction Data (ICDD) database (volumes 1-45).

a) Calcium Phosphate Fillers (i) Reactive Fillers

The calcium phosphate mixture consists of equimolar sintered β-tricalcium phosphate (β-TCP) and monocalcium phosphate monohydrate (MCPM—Rhodia, Birmingham, UK) with median final particle sizes of 11 and 62 μm respectively (as determined by laser diffraction particle sizing).

β-TCP was prepared by sintering a 2:1 molar mixture of dicalcium phosphate anhydrous (DCPA, Mallinckrodt-Baker, Griesheim, Germany) and calcium carbonate (Merck, Darmstadt, Germany) at 1050° C. for 24 h followed by milling and sieving.

(ii) Phosphate Glasses

For $(P_2O_5)_{0.45}(CaO)_x(Na_2O)_{0.55-x}$ glass preparation, sodium dihydrogen orthophosphate ($NaH_2PO_4$), calcium carbonate ($CaCO_3$) and di-phosphorous pentoxide ($P_2O_5$) (BDH, U.K) were weighed (Table 1) and placed into a 200 ml platinum/10% rhodium crucible. The crucible was placed in a furnace (Carbolite, RHF 1600, UK) initially at 300° C. for 30 min, then at 600° C. for 30 min and finally at 1050° C. for one hour. The resultant glass was poured onto a stainless steel plate, ground into powder form when cooled into solid, and sieved to obtain a particle size range between 20 and 45 μm.

TABLE 1

Amounts of precursors used for preparation of the two phosphate glass.

| Glass system | $NaH_2PO_4$ (g) | $CaCO_3$ (g) | $P_2O_5$ (g) |
|---|---|---|---|
| $(P_2O_5)_{0.45}(CaO)_{0.30}(Na_2O)_{0.25}$ | 30.04 | 15 | 14.17 |
| $(P_2O_5)_{0.45}(CaO)_{0.40}(Na_2O)_{0.15}$ | 18.03 | 20 | 21.28 | b) Poly(Lactide Co Propylene Glycol Co Lactide) Dimethacrylate Monomer (PPGLADMA):

The monomers were synthesised and characterised as previously described (Young et al, Eur. Polymer J., 2006, 42(8), 1775). To prepare P17L4, polypropylene glycol (PPG, $HO[CH(CH_3)CH_2]_7OH$, molecular weight of 1000 g/mol, Aldrich) was reacted with d-l lactide ($C_6H_8O_4$, Aldrich) in a molar ratio of 1:4 under vacuum at 150° C. and a nitrogen atmosphere for 6 hours, using stannous octoate (0.05% (w/w) of PPG) as an additional catalyst. After purification in propan-2-ol the resultant poly (propylene glycol-co-lactide) was redissolved in dichloromethane and methacrylate groups attached through reaction with triethylamine, and methacryolyl chloride at 0° C. both at 4 mol/mol of intermediate. The resultant monomer was purified using acetone followed by hexane (yield=67%). Other degradable polymers were prepared using PPG of molecular weight 425 or 2000 g/mol and PPG:lactide in the molar ratio 1:2 or 1:8.

The monomer structure was confirmed using ATR-FTIR and Raman spectroscopy $^1$H-NMR.

IR: $v_{max}$ (cm$^{-1}$) 2940 and 1452 (ester and ether C—H), 3110 and 1407 (Raman only) or 1155 (FTIR only) (methacrylate C—H), 1745, 1678 and 1719 (ester and methacrylate C=O respectively), 1088 and 1184 (ether and ester C—O respectively) and 1640 cm$^{-1}$ (methacrylate C=C).

$^1$H-NMR: δ (ppm) 1.13 (ether —CH$_3$), 1.54 (ester —CH$_3$), 1.95 (methacrylate —CH$_3$), 3.54 (ether —CH— and —CH$_2$—), 5.11 (ester —CH—) and 5.64 and 6.21 (methacrylate —C=CH).

Methacrylate end capping efficiency from the relative areas for the 1.13 and 5.64 with 6.21 ppm peaks was calculated as 103%.

Efficiency of lactide attachment to the PPG from the peak areas at 1.54 and 1.13 ppm was 97% of that expected.

c) Composite Formulations

First comparative formulation F1 (containing no filler) and second and third comparative formulations F2 and F3 (containing $(P_2O_5)_{0.45}(CaO)_x(Na_2O)_{0.55-x}$, where x=0.3 and 0.4 respectively) were prepared.

Formulation F4 was prepared according to the present invention, and contained an equimolar mixture of β-TCP and MCPM as a reactive filler.

The filler/liquid ratio for all the composites was 2:1 by weight, which was sufficiently low to ensure all samples were fluid prior to polymerisation. In all samples the liquid phase consisted of the PPGLADMA monomer, combined with 1 wt % of each photoinitiator-camphorquinone (CQ, 99%) and N,N dimethyl-p-toluidine (DMPT) and 10 wt % hydroxyethyl-methacrylate (HEMA) (to aid dispersion of the initiators). CQ, DMPT and HEMA were obtained from Sigma Aldrich.

To prepare solid discs for degradation studies, filler monomer pastes were placed into steel rings of 8 mm diameter and 1 mm depth. With the top and bottom surfaces covered with acetate sheets these were then placed into a light box (Densply Trubyte Triad® 2000™ visible light cure system) and crosslinked using 10 mins exposure (sufficient for >98% cure for all samples) of blue light (100 mW/cm$^2$) before removal from the ring.

Example 1

Composite Polymerisation/Set

To confirm that fillers can be incorporated within formulations without preventing crosslinking polymerisation of the methacrylate groups, formulations were prepared with 0:1 or 2:1 filler to monomer ratio.

Method: Three samples of each unset formulation were placed in a 1 mm deep ring maintained at 37° C. They were then exposed to blue light (400 mW/cm$^3$) for 80 s and FT-IR spectra were obtained every 23 s for 40 minutes. The final polymerisation percentages for formulations F1 to F3 were determined by comparing the height of the Raman methacrylate C=C 1640 cm$^{-1}$ peak (in background subtracted and 2900 cm$^{-1}$ peak normalised spectra) before and 24 hours after curing. With F4 this had to be estimated from a weaker FT-IR 1640 cm$^{-1}$ peak because of its high fluorescence Raman background. The percentage reaction as a function of time was then obtained by combining final percentages with the FTIR absorbance change variation with time at 1716 and 1734 cm$^{-1}$ using the method detailed in Young et al (*European Polymer Journal*, 2006, 42(8), 1775). Maximum reaction rate for each formulation was determined from the gradient of the calculated polymerisation percentages between 15 and 85 s.

Results: As can be seen from Table 2, although scattering by the fillers can reduce light penetration into the specimen and thereby slightly reduce initial polymerisation rate of the composite, with 80 s light exposure time over 90% conversion of the methacrylate monomers is obtained at 24 hours post light exposure with both the unfilled polymer and composites.

TABLE 2

Polymer and composite rate and extent of polymerisation with 80 s of blue 400 mW cm$^3$ light exposure determined using a combination of Raman and FTIR spectroscopy.

| Formulation number | Inorganic filler | Average filler particle size (μm) | Maximum polymerisation rate (%/s) | Polymerisation at 80 s (%) | Polymerisation at 24 h (%) |
|---|---|---|---|---|---|
| F1 | None | — | 1.5 | 85 | 94 |
| F2 | $(P_2O_5)_{0.45}(CaO)_{0.30}(Na_2O)_{0.25}$ | 35 | 1.5 | 88 | 99 |
| F3 | $(P_2O_5)_{0.45}(CaO)_{0.40}(Na_2O)_{0.15}$ | 35 | 1.2 | 80 | 97 |
| F4 | β-TCP and MCPM | 11 and 62 | 0.85 | 60 | 92 |

Example 2

Polymer Degradation in Water

To assess water sorption and degradation of the polymer and composite, samples of fully polymerised material discs 8 mm diameter and 1 mm depth were placed in water and their water content, filler and polymer loss determined via gravimetric and density studies as a function of time.

Method: Specimens of each formulation of known initial mass, $m_0$ (average of 72 mg for F1 and 120 mg for the composites) were placed upright in the conical end of an individual sterilin tube, allowing contact with water (10 cm$^3$ adjusted to pH 7 and incubated at 37° C.) on all sides. For all samples the water was exchanged at 0, 0.5, 1, 2 and 4 hours, 1, 2, 4, 7 and 10 days as well as 2, 3, 4, 7 and 10 weeks.

a) Volumetric and Density Changes

At all the above time points, three specimens of each formulation were removed from the tube, the external surface blotted dry with tissue paper and their mass, volume and density assessed gravimetrically before placing back into fresh pH-adjusted deionised water. The volume was converted to total change as a percentage of initial values using the formula:

$$\Delta V_t(\%) = 100 * [(V_t - V_0)/V_0] \qquad 1$$

where, $V_t$ and $V_0$ respectively, are volume of the specimen at time t and time 0. The standard deviation divided by the value of volume change or density was approximately constant for all samples (excluding the first data point which has a significantly larger error in most of the measurements) and on average equal to 0.2 or 0.02 respectively (equivalent to 20 or 2% error). The large error on the volume change is counteracted by its determination at many time points and fitting of trend lines through the data. Assuming then the density of a mixture is the sum of the total mass divided by the total volume of the individual components it will be given by $$\frac{1}{\rho} = \sum \frac{x_i}{\rho_i} \qquad 2$$

where $x_i$ and $\rho_i$ are the mass fraction and density of each pure component in the mixture. Additionally $$\Sigma x_i = 1 \qquad 3$$

In this study i has values of 1, 2 and 3 each representing the polymer, filler and water respectively. Using equations 2 and 3 with the densities of the polymer and composites prior to their submersion in water an average density of the inorganic fillers was obtained.

b) Compositional Changes and Mass Loss

The dry mass (after vacuum drying to constant weight) of three specimens of each formulation were determined at 1 and 3 days and 1, 2, 7, 9 and 10 weeks and fractional water content, $x_3$ calculated by comparison with the final wet mass. The standard deviation of $x_3$ divided by its value (after the first time point) had an average value of 0.05 (i.e. 5% error). Expanding, combining and rearranging equations 2 and 3, it can be shown that the fraction of polymer left in the composite at a given time, $x_1$, can then be calculated using the densities of the composite, $\rho$ and pure components $\rho_i$, with $$x_1\left[\frac{1}{\rho_1} - \frac{1}{\rho_2}\right] = \left[\frac{1}{\rho} - \frac{1}{\rho_2}\right] - x_3\left[\frac{1}{\rho_3} - \frac{1}{\rho_2}\right] \qquad 4$$

Again the subscripts 1, 2 and 3 represent polymer, filler and water respectively. Once $x_1$ and $x_3$ are known the fraction of glass in the composite, $x_2$ at a given time can be calculated from equation 3. The fraction of dried composite that is polymer, $y_1$ and glass $y_2$ is then given by $$y_1 = \left[\frac{x_1}{x_1 + x_2}\right] \qquad 5$$

and $$y_2 = 1 - y_1 \qquad 6$$

Total mass loss fraction, z, (with on average 3% error) was calculated by comparison of the final dry masses with initial dry mass. From z and mass balance the mass fraction of polymer $z_1$ (or filler $z_2$) from the original composite that has dissolved is then obtained using $$z_i = 1 - \frac{y_i}{y_{i,0}}(1 - z) \qquad 7$$

With i equal to 1 or 2 and $y_{i,0}$ the initial fraction of polymer or filler in the composite.

Results: From FIG. 1a it can be seen that long term water content of the composite of the invention (F4) is greater than that of the polymer alone (F1).

Figure 1:
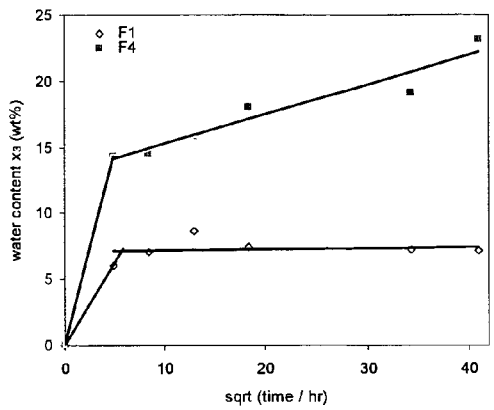
FIG. 1: Degradable polymer and composites water content, and polymer and filler loss, as a function of the square root of time over a period of 10 weeks.
a) water content of polymer F1 and reactive filler composite F4
b) polymer and filler loss of polymer F1 and reactive filler composite F4
c) water content of polymer F1 and composites F2, F3 (phosphate glass fillers) and F4 (reactive filler)
d) polymer and filler loss of polymer F1 and composites F2, F3 (phosphate glass fillers) and F4 (reactive filler).
Figure 1:
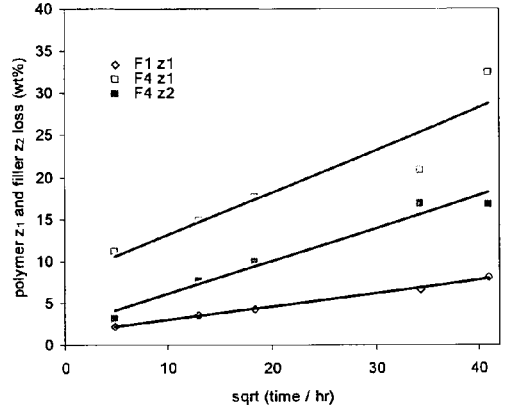
Figure 1:
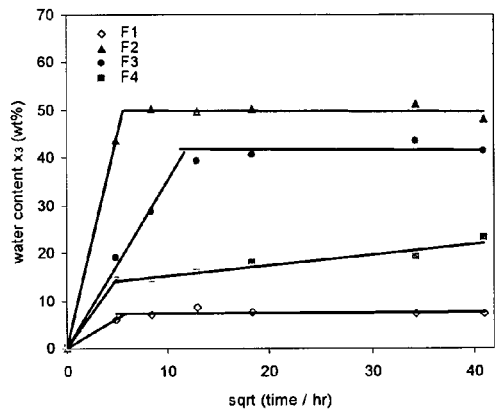
Figure 1:
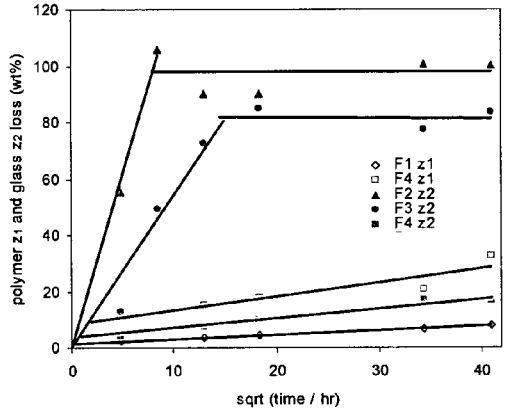

FIG. 1b shows that rate of polymer loss is also observed to be much faster for the composite (F4) than polymer (F1), thereby providing a simple means to raise the rather slow pure polymer degradation rate.

In both cases, unlike with conventional polyesters, the degradation occurs immediately upon placement in water indicating that it is most probably occurring from the surface. The polymer degradation rate decreases with time as the surface composition alters.

The present inventors have previously shown (*Eur. Polymer J.*, 2006, 42(8), 1775) that through changes in monomer molecular weight, polymers that degrade linearly with time over 10 weeks may be generated. Varying the levels of filler particles in the compositions of the present invention may therefore provide a way to control the rate of degradation of the polymers.

It can also be seen from FIG. 1b that after an initial burst release of acid, rates of acid and filler loss are comparable. This equal rate loss of components can be beneficial as it means there is no sudden decrease in mechanical properties due to catastrophic bulk degradation (caused by acid build up or removal of filler leaving behind a weakened polymer). It is thought that the initial fast release of the polymer arises because the surface of a flat composite specimen will have a higher fraction of the matrix than the bulk because only the top or bottom edge of a spherical particle can be at a flat surface. The release of filler and polymer together after this surface degradation is believed to be a consequence of the particles being dispersed within the polymer matrix in a poorly soluble but finely dispersed brushite form which can only be released with the degraded polymer within which it is entangled. By comparison the highly soluble phosphate glasses can diffuse through the polymer and be released before the surrounding polymer.

Figure 2:
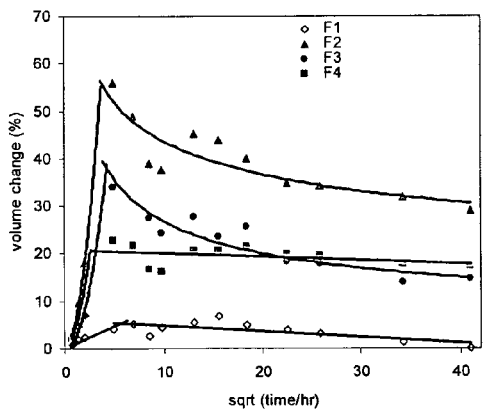
FIG. 2: Effect of (square root of) time in water on the volume of the degradable polymer F1 and composites containing phosphate glasses (F2 and F3) or the reactive filler (F4).

The dimensional (volumetric) stability of the composites is compared in FIG. 2. The reactive filler composite of the invention (F4) is dimensionally stable after an initial expansion. Comparative examples F2 and F3 show much greater water-induced expansion.

Example 3

Sample Storage Solution Composition

Method: Cumulative storage solution acid content per specimen, $C_a$ was calculated assuming $$pH = -\log[H^+] \qquad 8$$

and $$C_a = \sum_0^t [H^+]_t \qquad 9$$

$[H^+]$ is the molar hydrogen ion concentration. For the polymer, the average standard deviation for cumulative acid release was 12%. Provided acid released from the polymer is not neutralised and the same degradation process is occurring at all times $C_a$ should be proportional to the mass of polymer eroded and given by $$C_a = \frac{m_0}{MV} z_1 \qquad 10$$

$m_0$, V and M are the initial sample mass, storage solution volume and average mass per acid group of the eroded polymer fragments.

Other ion release, both cation and anion, into these storage solutions up to 2 weeks was additionally monitored. Analysis of all solutions was completed within 30 minutes from the end of the sample storage period. The average error for all ion release determined using this technique was 8% (excluding data in the first 4 hours).

For the phosphate-glass composites four of the anionic species formed as a result of the breakdown of the $P_2O_5$ network-forming backbone were quantified. These were namely, $PO_4^{3-}$ (orthophosphate), which is the smallest phosphate species formed as a result of the hydrolysis of the P—O—P bonds; $P_2O_7^{4-}$ and $P_3O_{10}^{5-}$ (linear polyphosphates), formed as a result of hydration of the phosphate chains; and $P_3O_9^{3-}$ (cyclic trimetaphosphate). Calibration was obtained with standard solutions containing 1, 10, 25 and 50 ppm of sodium phosphate tribasic ($Na_3PO_4$), trisodium trimetaphosphate ($Na_3P_3O_9$), pentasodium tripolyphosphate ($Na_5P_3O_{10}$) (Sigma) and tetrasodium pyrophosphate ($Na_4P_2O_7$) (BDH). Results were converted to mM (of phosphorus) per specimen to allow comparison with acid release and with the total phosphorus calculated from initial compositions originally in the samples. With composites of F4, $PO_4^{3-}$ is the only anion expected.

Figure 3:
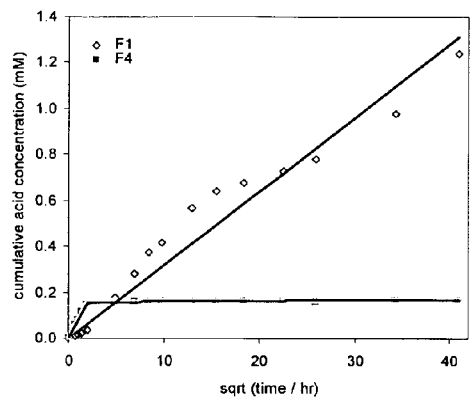
FIG. 3: Cumulative acid level and phosphate and calcium release as a function of the square root of time from the degradable polymer and composites.
a) cumulative acid concentration for polymer F1 and composite F4
b) cumulative ion release (Ca and P) for composite F4
c) cumulative acid release for polymer F1 and composites F2, F3 and F4
d) cumulative ion release (Na and Ca) for composites F2, F3 and F4
e) cumulative ion release (P) for composites F2 and F3.
Figure 3:
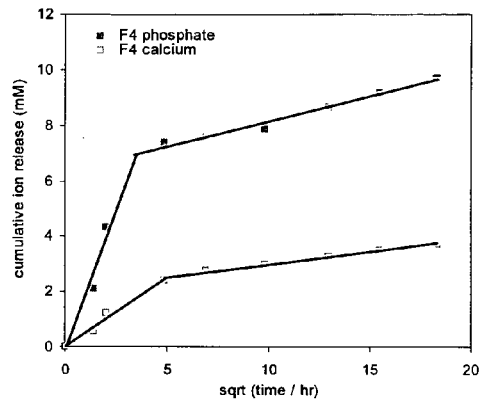
Figure 3:
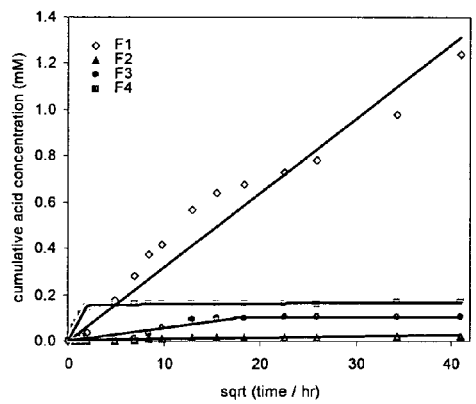
Figure 3:
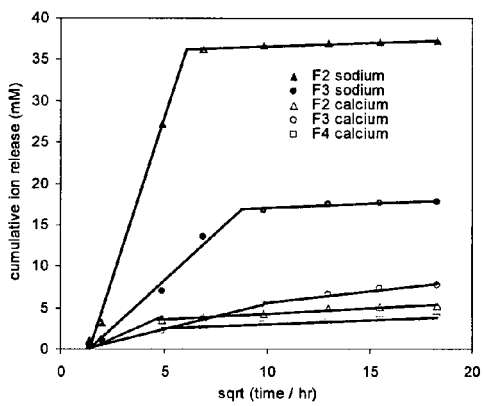
Figure 3:
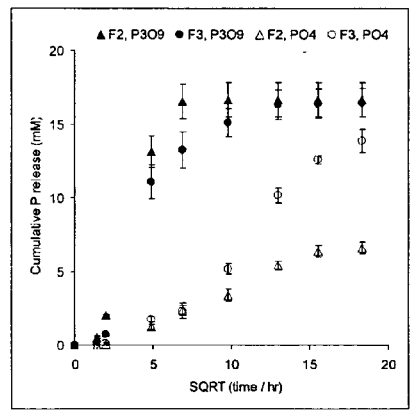

Results: With polymer degradation there is a decrease in the pH of the medium in which the specimens are stored. From FIG. 3a it can be seen that the level of acid generated (determined from pH measurements) from composite (F4) after the initial burst polymer release is very much less than that from the pure polymer (F1). In FIG. 3b cumulative phosphorus and calcium contents of the composite sample storage solutions determined via ion chromatography are also given. The total levels of these ions are consistent with that expected from the gravimetric studies although the ratio of phosphorus to calcium is higher than in the filler.

The combined gravimetric and storage solution studies are all consistent with the filler acting as a buffer and some of the calcium ions being bound with neutralised polymeric degradation products. Acid buffering by fillers has previously been shown to be advantageous reducing inflammatory responses in the body. It may also reduce the possibility of sudden catastrophic core degradation of the material caused by acid build up.

Example 4

Mechanical Properties a) Surface Hardness

Method: Indentation depth for the polymer F1 and composite F4 were determined in water using a Wallace hardness indentation test at the following time points: 0, 10 and 30 mins, 1, 2, 2.5 and 18 hours, 1, 2, 3, 6, 10 and 13 days. A specimen of each formulation was placed in 10 ml deionised water incubated at 37° C. At each time point, the specimen was removed from the water and blotted dry with tissue paper. A 300 g load using a Wallace indentation hardness tester was applied onto the surface of the specimen and the indentation depth measured. Eight readings, four on each side of the specimen, were taken.

b) Material Modulus

Method: At 0 and 4 hours, 1, 3, 6 and 9 days and 2, 3, 7 and 10 weeks the specimens used in the volumetric investigations above were additionally tested using dynamic mechanical analysis. A parallel plate set-up was used, incorporating a 3 mm probe, with a static force of 5 mN and a superimposed dynamic compressive force of 4 mN at a frequency of 1 Hz. Testing was carried out at 25° C. for 60 s, and storage and loss modulus recorded at 30 s. Standard deviations for samples F1, F2 and F3 were on average 60% after the first 24 hours but much lower at only 5% for F4.

Figure 4:
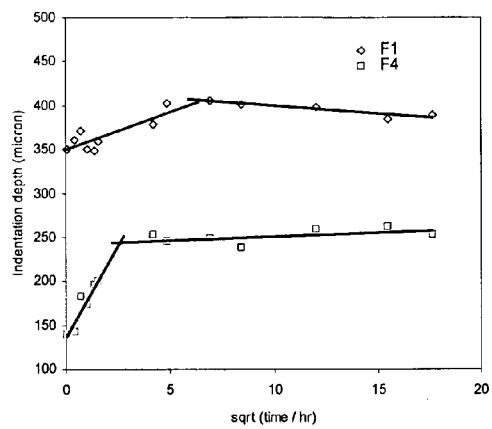
FIG. 4: Degradable polymer F1 and composites Wallace hardness indentation depth, and loss and storage modulii as functions of the square root of time.
a) indentation depth for polymer F1 and composite F4
b) dynamic modulus for polymer F1 and composite F4
c) indentation depth for polymer F1 and composites F2, F3 and F4
d) storage modulus for polymer F1 and composites F2, F3 and F4.
Figure 4:
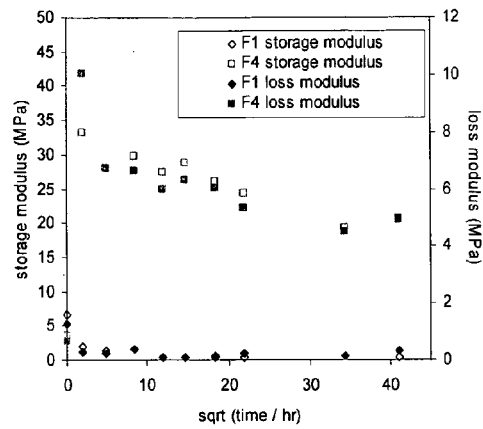
Figure 4:
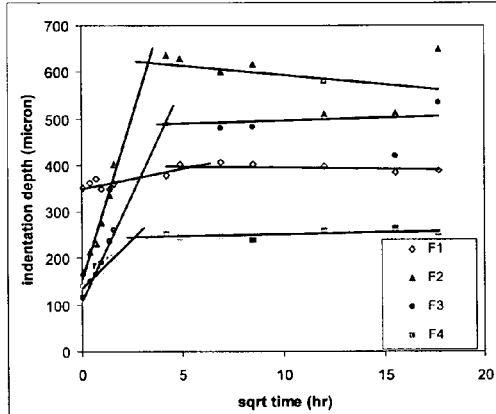
Figure 4:
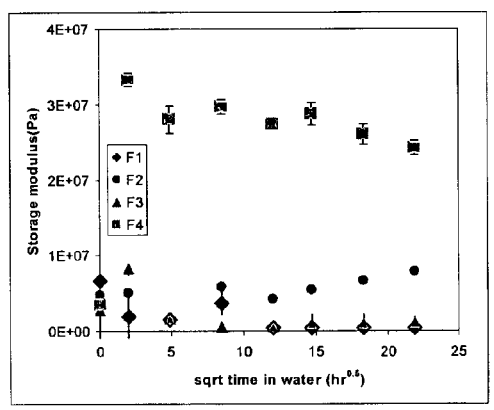

Results: In FIG. 4a indentation depth (determined using a Wallace hardness indentation test for the polymer (F1) and the composite of the invention (F4) is shown. The level of penetration of the weight into the specimen is much greater with the polymer than the composite. The initial increase in depth with time (consistent with a decrease in surface hardness) for the composite can be explained by water sorption. After the first 24 hours, however the surface hardness becomes stable with further water sorption having limited effect.

As shown in FIG. 4c, comparative examples F2 and F3, with phosphate glass fillers, show an initial increase in hardness, but further water sorption and degradation cause a subsequent decrease to hardness levels below that of the polymer alone.

More dramatic, however, is the effect of water sorption on material modulus. From FIG. 4b it can be seen that, upon placement in water, the modulus of the reactive filler composite samples increases by an order of magnitude as the material changes from a flexible to a less flexible solid. In comparison, from FIG. 4d, it can be seen that with phosphate glass fillers (comparative examples F2 and F3) the modulus remains low.

These results demonstrate how materials with a broad range of mechanical properties, for different applications, may be obtained from the compositions of the present invention, by using varying levels of reactive filler particles:

Example 5

Changes in Material Chemistry

Method: Raman chemical surface maps of sample F4 were obtained initially, and after 2 and 4 days in water.

Reference spectra of the individual initial components and of brushite (formed by reaction of equimolar β-TCP and MCPM with water) were obtained over the same wavelength range to aid component identification in the maps. Dominant polymer peaks were observed at 871 and 1455 $cm^{-1}$ (C—H stretch). The phosphate glasses had two relatively broad but intense peaks at 693 and 1168 $cm^{-1}$. β-TCP had double sharp PO stretch peaks at 948/971 but with MCPM these shifted to 903/915 $cm^{-1}$. Brushite had a dominant sharp peak at 990 $cm^{-1}$ and from the literature that of the anhydrous form Monetite is expected to be similar.

Figure 5:
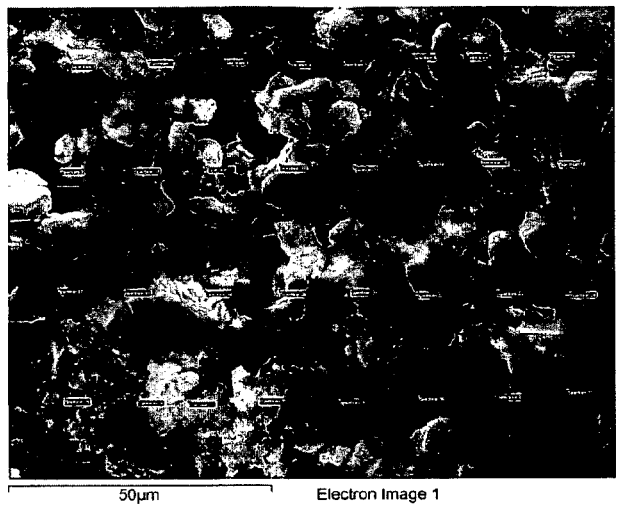
FIG. 5: Example SEM images of sample F4 (blue lines are points of EDAX analysis for Table 2) a) dry and b) after 2 weeks in water.
Figure 5:
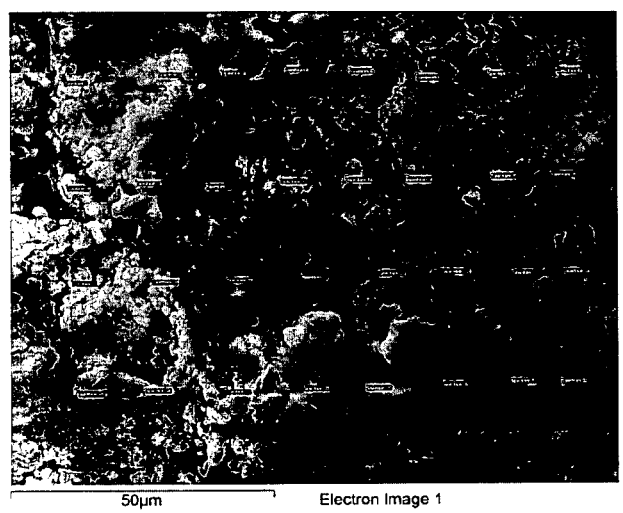

Results: The β-TCP and MCPM particles in the composite F4 disappear with time in water. From SEM it can also be seen that after placement in water the particles in the composite are finer (see FIG. 5). From EDAX with SEM the P/Ca ratio although not significantly different on average throughout the composite is observed to have a much narrower standard deviation as expected with reaction of β-TCP and MCPM to form brushite (see Table 3). In the dry sample particles can readily be assigned as either β-TCP or MCPM as the P/Ca ratio tends to 1.5 or 0.5 respectively at any given point but not in the composite where most regions have this ratio close to 1 as expected for brushite.

Figure 6:
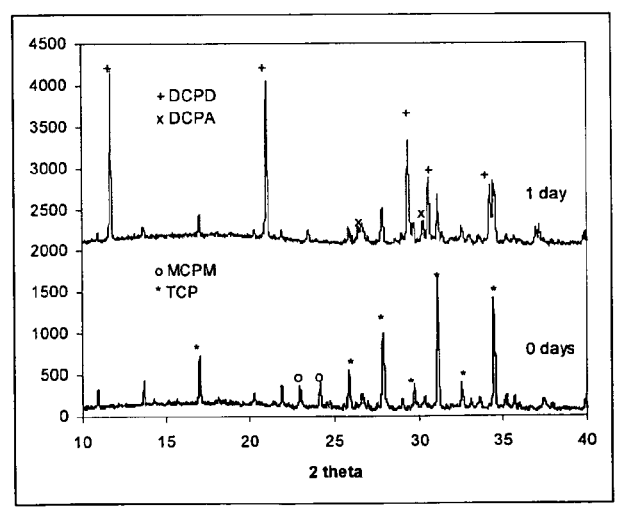
FIG. 6: XRD spectra of composite specimen F4 initially and after 24 hours in water proving formation of brushite upon water sorption.
Figure 7:
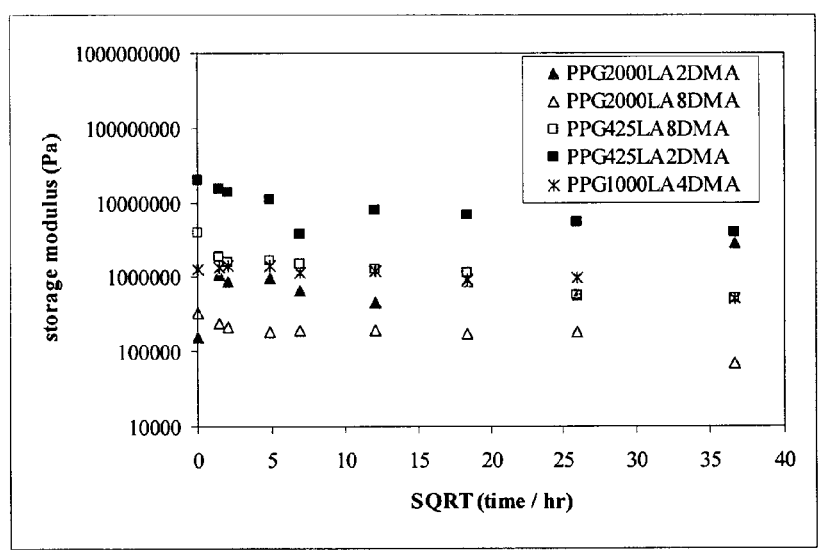
FIG. 7: Storage modulus of degradable polymers demonstrating order of magnitude increase with a reduction in monomer molecular weight (Batch lot no. 180803).

From X-ray diffraction data it is also clear that within 24 hours a large proportion of the fillers in the composite are converted into brushite (see FIG. 6). These chemical changes and better dispersion of the calcium phosphate throughout the composite are consistent with the changes in mechanical properties observed above. They should also improve various other mechanical properties (eg. wear resistance).

TABLE 3

Average P/Ca elemental ratios for samples kept dry or in water for 2 weeks and their standard deviations obtained using SEM with EDAX (values in brackets are 95% confidence intervals obtained using 5 images (see for example FIG. 5) for each specimen)

|     | average |        | stdev |        |
|-----|---------|--------|-------|--------|
| dry | 0.99    | (0.08) | 0.52  | (0.04) |
| wet | 0.91    | (0.03) | 0.21  | (0.03) |

Example 6

Raman Mapping of Chemical Changes

Raman mapping studies were repeated, with the top surfaces of the samples removed prior to analysis.

Method: A Raman map of the sample F4 was generated before and after immersion in water for 18 hours using a LabRam spectrometer (Horiba Jobin Yvon) with a 633 nm laser, ×50 objective and 1800 grating over a wavenumber range of 700 to 1600 $cm^{-1}$. Prior to analysis of either the dry or wet sample the top approximately 300 micron layer was removed with a razor to gain spectra and images representative of the sample bulk. Areas 200 by 200 micron square were analysed using a step size, of 5 micron. The average spectra and those at individual points were compared with raman spectra of MCPM, βTCP, P17L4 polymer and brushite cement (formed by reacting MCPM and βTCP with water). To generate maps of chemical homogeneity/structure, modelling software with the LabRam was used.

Figure 8:
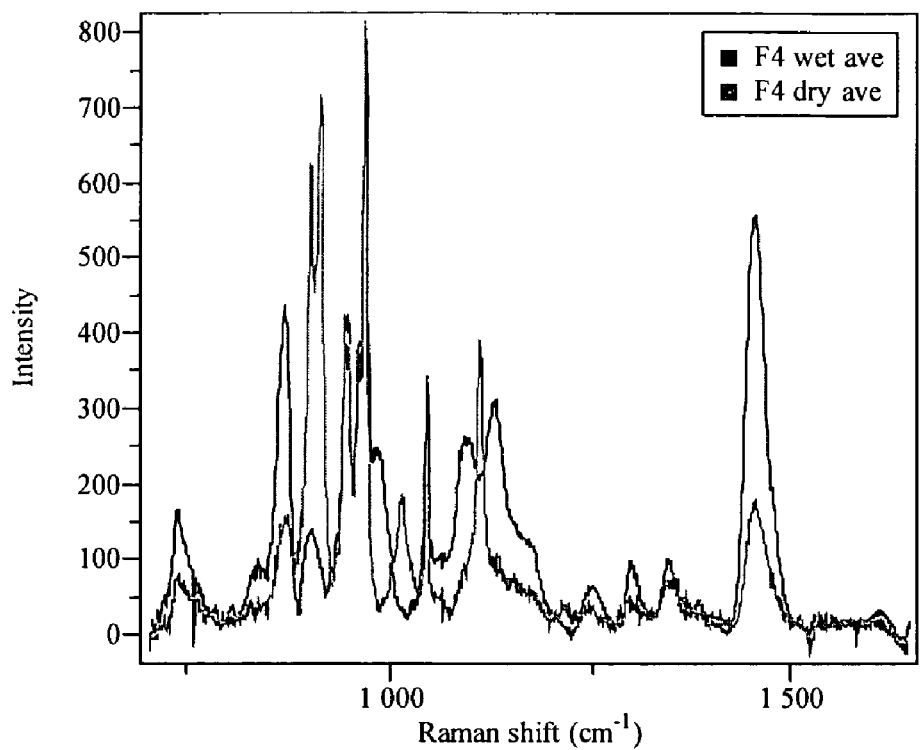
FIG. 8: Average Raman spectra of sample F4 before and after immersion in water for 18 hours.
Figure 9:
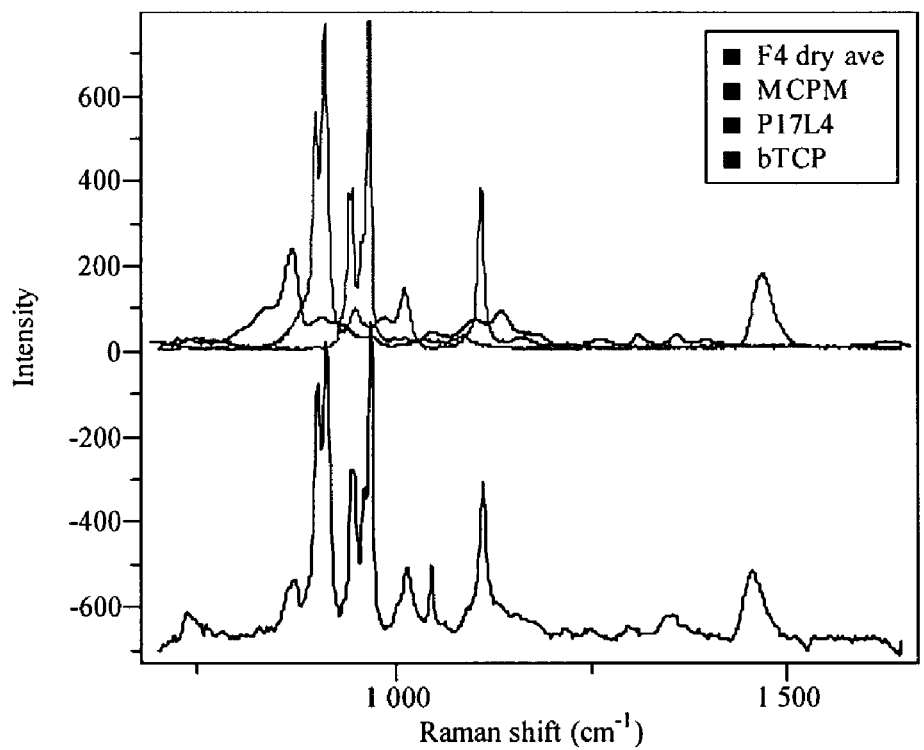
FIG. 9: Comparison of the average spectrum of the dry F4 sample with that of MCPM, β-TCP and the degradable polymer P17L4.

Results: FIG. 8 shows the average spectra of sample F4 before and after submersion in water. The average spectrum of the wet sample has stronger polymer peaks (1100 to 1600 $cm^{-1}$) relative to the MCPM and βTCP phosphate peaks (800 to 1050 $cm^{-1}$) indicating loss of these phosphates upon water immersion. As can be seen from FIG. 9, practically all the peaks in the average dry sample spectrum are due to MCPM, βTCP or the polymer. This is not the case for the average spectrum of the wet sample (see FIG. 10).

Figure 10:
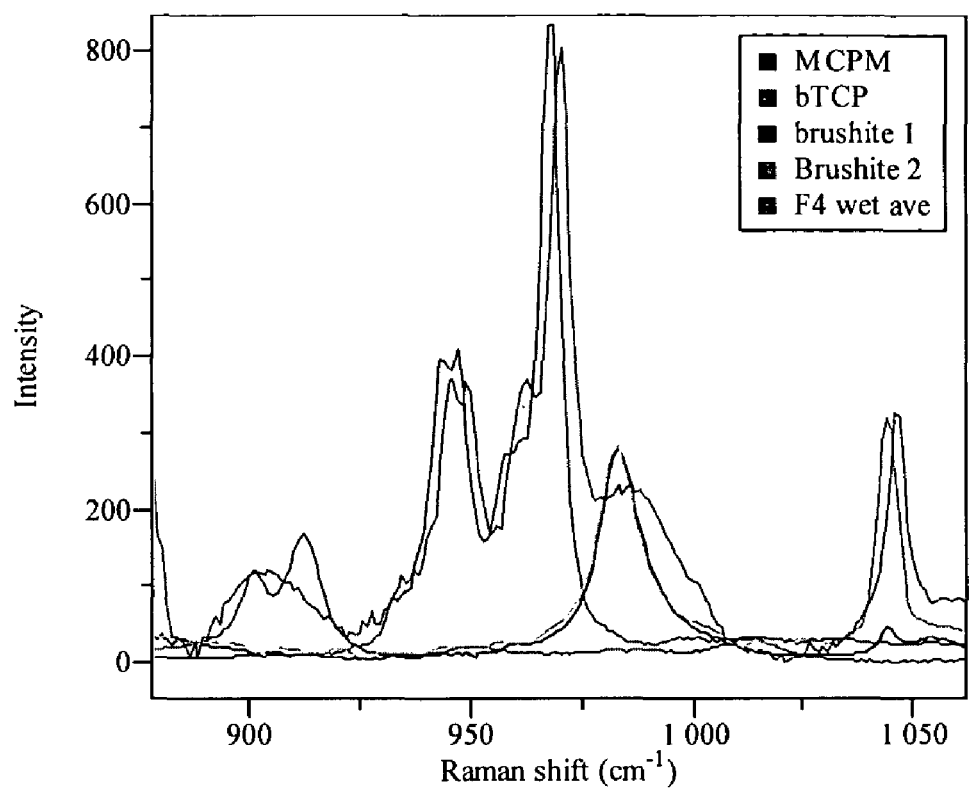
FIG. 10: Comparison of the average spectrum of F4 after immersion in water with that of MCPM, β-TCP and two spectra obtained from set brushite cement specimens further proving reaction of the fillers upon water sorption by the composite.

The spectrum of brushite cement was found to primarily have the spectrum brushite 1 given in FIG. 10. There were regions, however, with spectrum brushite 2 in FIG. 10. These differences in brushite spectra may be due to variations in crystal structure and orientation. Additional peaks in the average spectrum of the wet F4 sample are closer to those of the brushite 2 spectrum (see FIG. 10).

Figure 11:
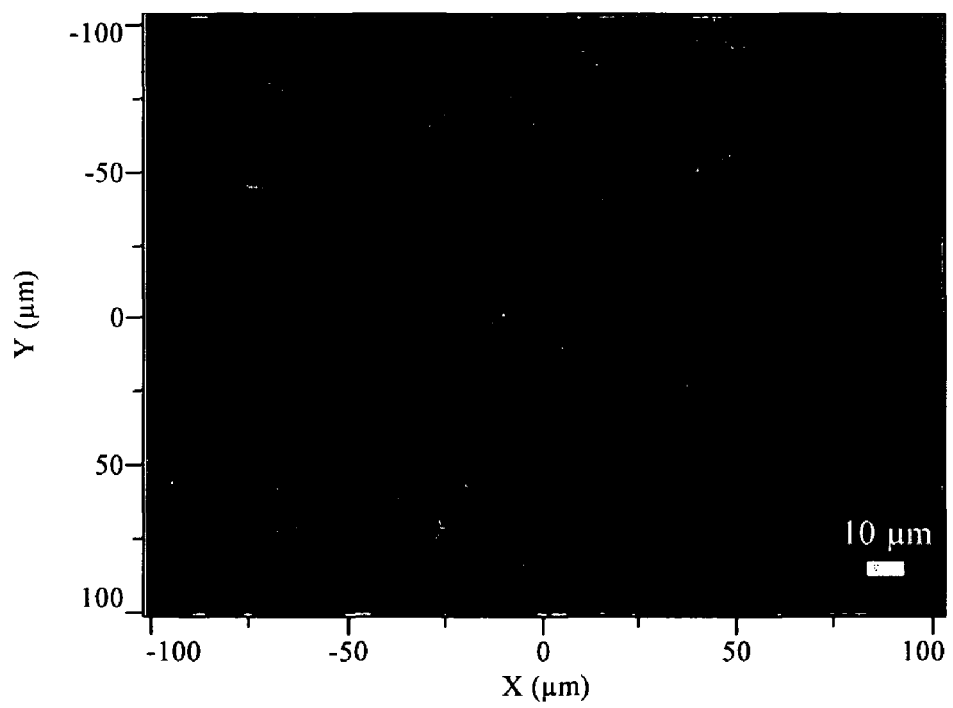
FIG. 11: a) Raman map of sample F4 dry modeled using b) raman spectra of β-TCP, MCPM and P17L4.
Figure 11:
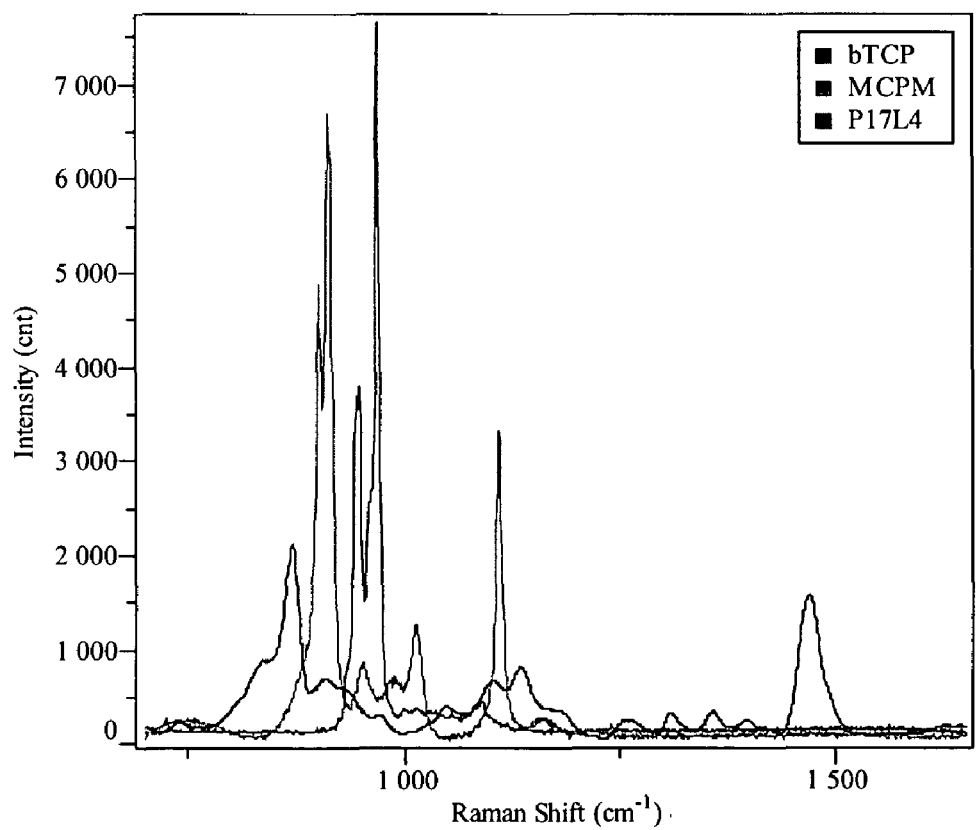
Figure 12:
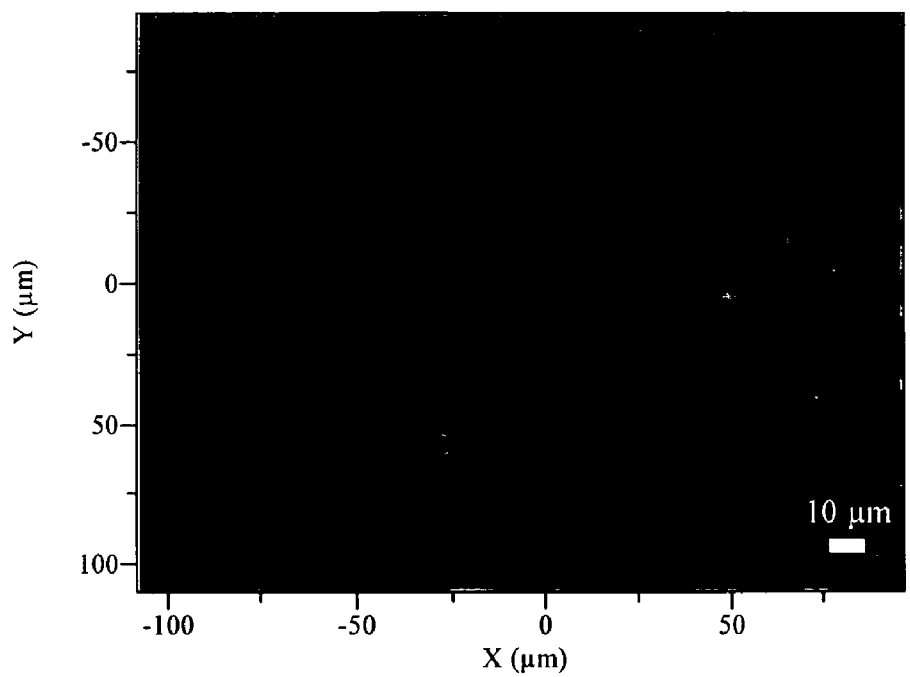
FIG. 12: a) Raman map of sample 4 after 18 hours in water modeled using b) raman spectra of β-TCP, average large particle spectrum and P17L4.
Figure 12:
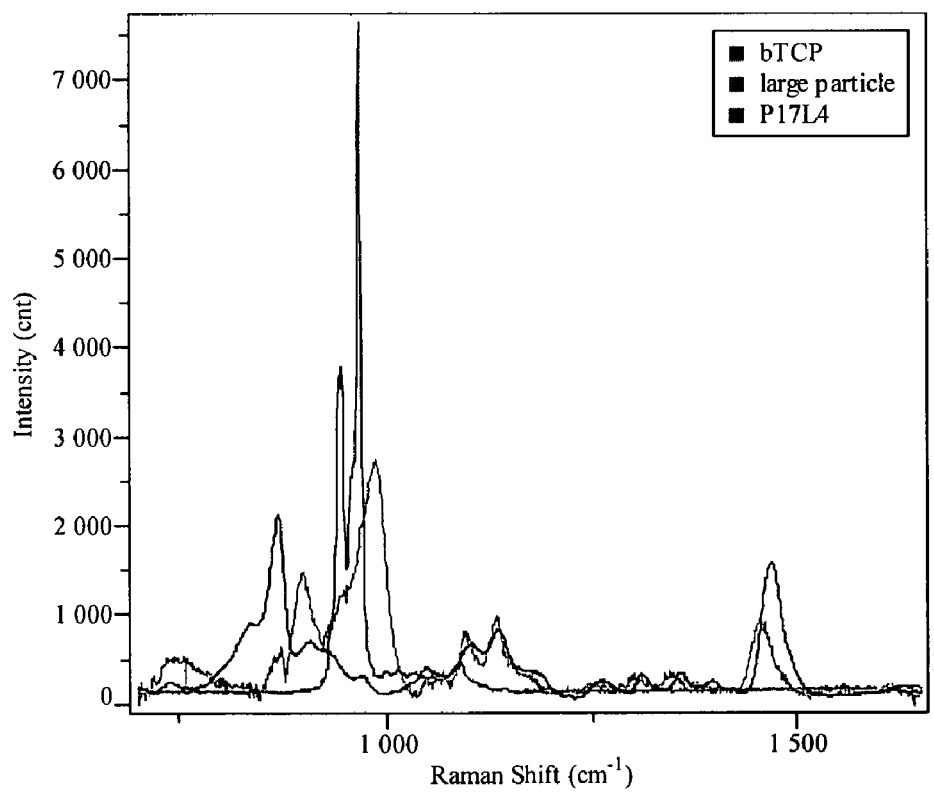
Figure 13:
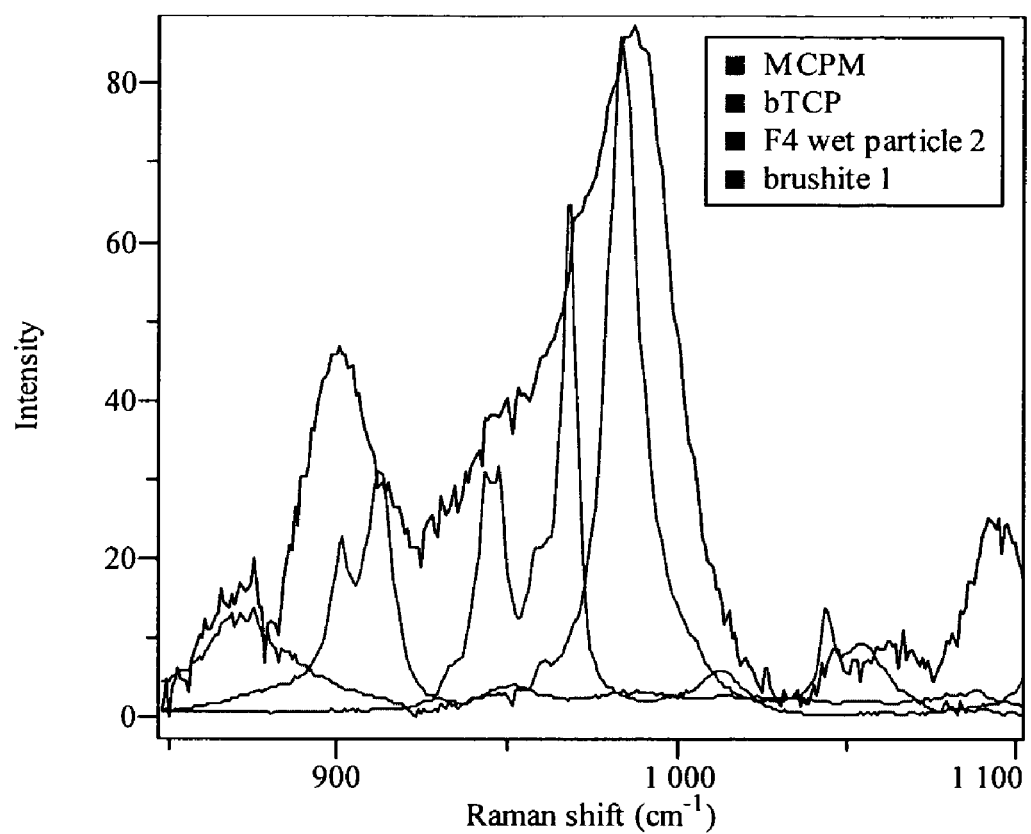
FIG. 13: Comparison of large particle spectrum in wet F4 sample with that of MCPM, βTCP and brushite showing that the larger MCPM particles have been replaced by a mixture of polymer and brushite.
Figure 14:
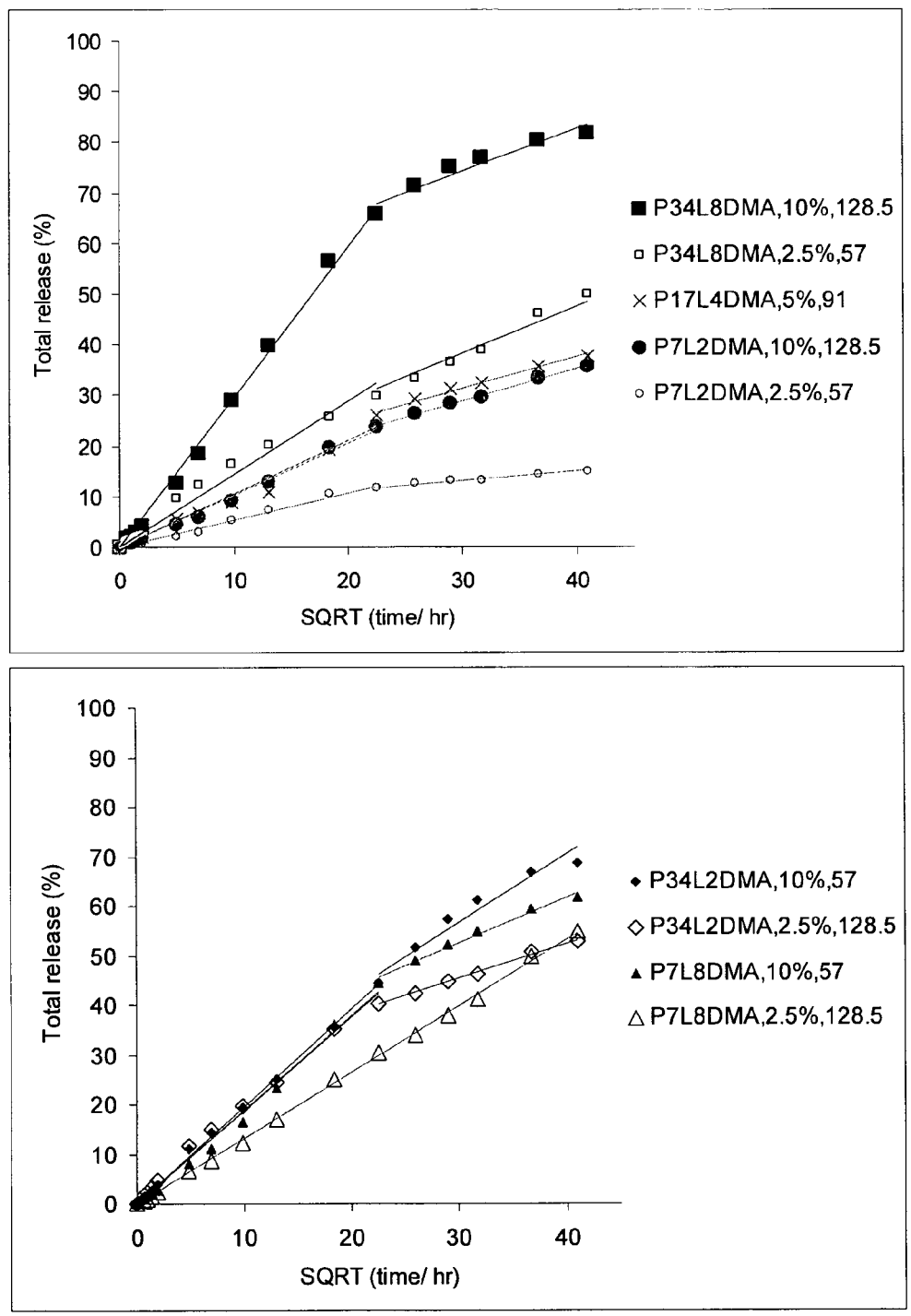
FIG. 14: Percentage drug release per specimen as a function of the square root of time for the degradable polymers containing the drug chlorhexidine diacetate. Filled and unfilled symbols represent 10 and 2.5 wt % drug levels in the polymer. Big and small symbols represent bigger (median size 128.5 μm) and small (median size 57 μm) size drug particles respectively. The "intermediate" formulation P17L4 contains 5 wt % drug. Results show that when the degradable monomer is short drug release is diffusion controlled but also limited to a maximum level well below 100%.
Figure 15:
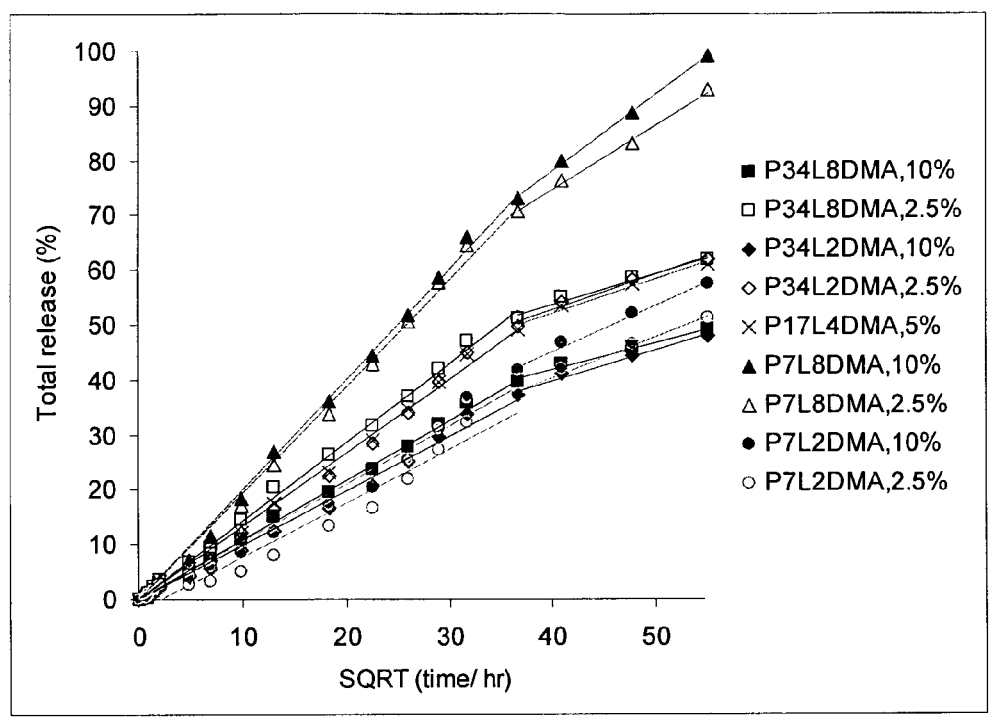
FIG. 15: Percentage drug release per specimen as a function of the square root of time for the degradable polymers containing the drug ketoprofen. Filled and unfilled symbols represent 10 and 2.5 wt % drug levels in the polymer. The "intermediate" formulation
P17L4 contains 5 wt % drug. Release kinetics are as expected for diffusion control.
Figure 16:
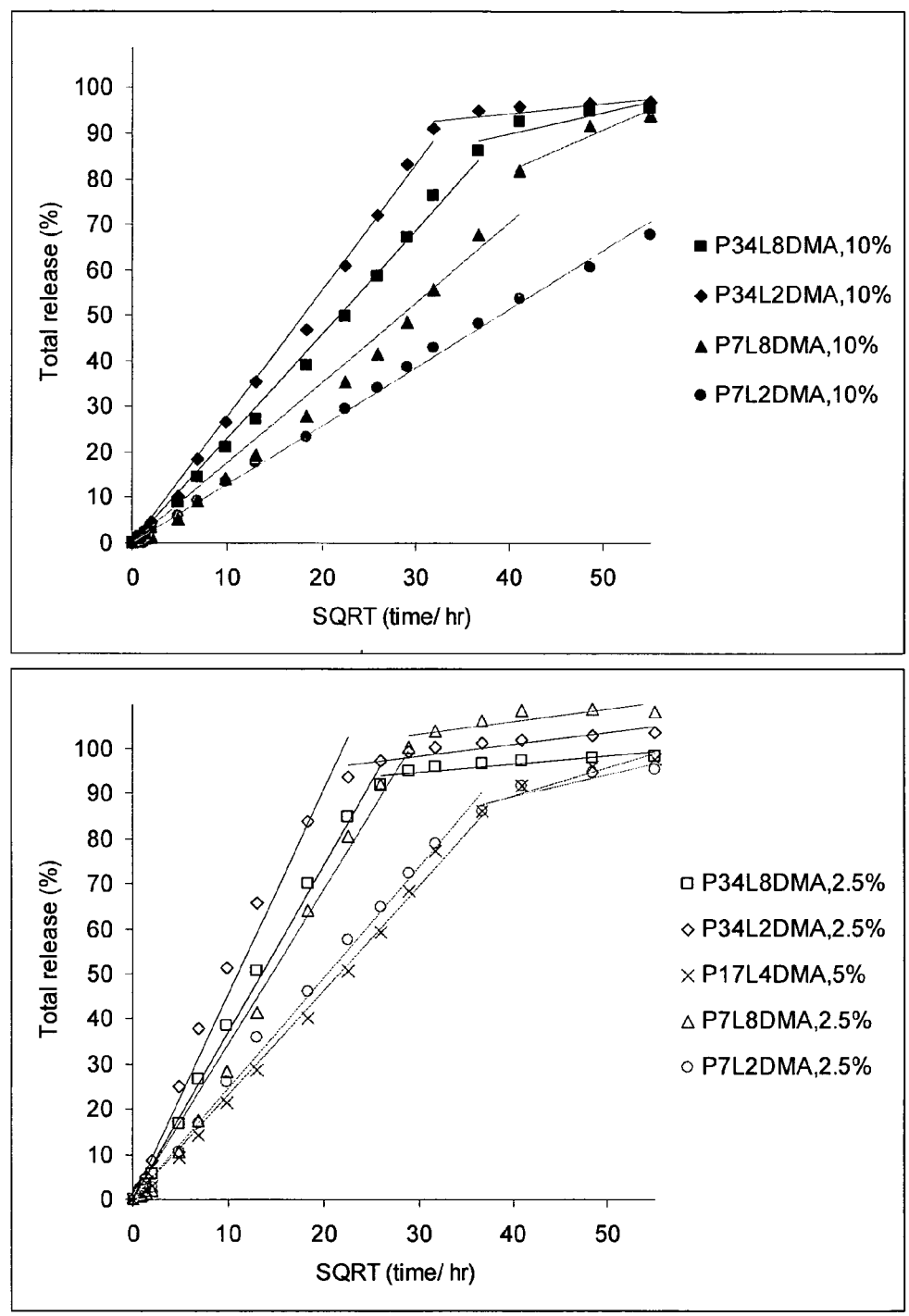
FIG. 16: Percentage drug release per specimen as a function of the square root of time for the polymers containing the drug prednisolone. Filled and unfilled symbols represent 10 and 2.5 wt % drug levels in the polymer. The "intermediate" formulation P17L4 contains 5 wt % drug.

FIG. 11a shows a Raman map of the dry F4 sample modeled using the spectra in FIG. 11b assuming there to only be MCPM, βTCP and the polymer P17L4 present. In the map the larger green MCPM and smaller red βTCP particles can clearly be differentiated from the blue polymer P17L4 matrix phase. After immersion in water large and small circular regions can still be observed within the blue polymer matrix phase (see FIG. 12). The spectrum of the green regions given in the FIG. 12a map, however, is no longer that of MCPM but that of a mixture of MCPM, βTCP and brushite (see FIG. 13). These green regions also contain, however, significant levels of the polymer P17L4 (see FIG. 12b). There is, in the wet F4 sample map, no region that can be assigned purely to MCPM, a reduction in the density of red βTCP particles and also various small (5 micron) as well as large (30 micron diameter) circular regions containing a mixture of all components. Since the resolution of the spectra at an individual point is of the order of 1 micron, in the green region the mixture of components must be homogeneous at this scale length.

The above results prove that after immersion in water the MCPM particles and to a lesser extent the βTCP particles have reacted to form regions homogeneous on the micron scale that contain both the polymer and brushite providing a mechanism for increased mechanical properties of the formulations.

Example 6

Preparation of DNA Delivery System a) Monomer Synthesis and Characterisation

Several fluid poly(lactide)-based dimethacrylate monomers as described above are synthesized, using poly(propylene glycol) (PPG) of molecular weight 400 to 2000 g/mol as a catalyst for ring opening polymerisation of lactide. Monomers of this type with average values of n between 2 and 8 have good monodispersity, reaction yields, fluidity and after set degradation rates that can be controlled over a broad range. To increase or decrease further polymer degradation rates, the lactide may be partially replaced by caprolactone and glycolide groups, respectively. Monomers containing 3 and 4 methacrylate groups can additionally be synthesised by replacing PPG (R in general formula (I)) with glycerol (HC $(OH)(CH_2OH)_2$) or pentaerythritol ($C(CHOH)_4$) respectively.

These can be used in combination with the other monomers to increase the level of crosslinking and thereby provide greater control over water sorption of the set formulations.

b) Monomer Based Microemulsions

The monomers from a) are used as the hydrophobic ('oil') phase of the reverse microemulsions. Pluronic/Tetronic surfactants (PEG co PPG copolymers which have previously been reported to enhance gene uptake (21)) can be dissolved (0.05 to 0.5M) in this dispersion medium to stabilise aqueous droplets (1 to 10 wt %) that contain DNA (1-100 μg/ml of water).

Upon inclusion of calcium chloride (1-5 wt %) and sodium hydrogen phosphate (0.2 to 1 wt %) to the aqueous droplet phase of the above microemulsions, upon ion exchange, nanoparticles will form dispersed in the continuous monomer phase. Other ions such as fluoride, hydroxide, acid or buffers may be added to the aqueous droplet phase to modify the calcium phosphate structure and solubility. Alternatively the above monomer reverse microemulsions are combined with particles of MCPM and TCP of varying diameter (1 to 200 micron) and powder to liquid ratio (0.1:1 to 4:1 by wt). Formulations are characterised before, during and after polymerisation using a combination of Raman and FTIR mapping spectroscopy to quantify rates of polymerisation and conversion of the MCPM and TCP particles to brushite around the DNA—containing water droplets. Degradation of the set/polymerised materials and release of components and nanoparticles in different fluids as a function of time and specimen dimensions may be assessed via a combination of gravimetric and Raman mapping studies of the solid specimens and ion chromatography, fluorescence, light scattering and biological investigations of the storage solutions.

c) "GeneCaP" Cell Transfer Optimisation

In initial experiments calf thymus (CT) DNA is fluorescent-tagged and converted to 8 kilobases by sonic disruption. The large amount of this material which is available will enable a very wide range of chemical formulations to be optimised for their cell transfer ability. Cellular studies will be carried out, first using normal murine fibroblasts for screening of large numbers of formulations. Correlation will be made between fluorescence-labelled CT DNA uptake and cell compatibility with the chemical and physical properties of the materials. Cell proliferation will be monitored using, a fluorescence assay such as Alamar Blue, and total DNA uptake and distribution per cell assessed using FCM, at various incubation times in the presence of systematically varying formulations. Fluorescent/confocal microscopy will be utilised to visualise surface versus internalised DNA. For quantitative purposes cell membranes will be disrupted using the non-ionic detergent NP40 and nuclear uptake assessed after centrifugation to separate the intact nuclei from the cytoplasmic/membrane compartments. Additionally, the kinetics of GeneCaP attachment to the cell surface will be assessed by incubating the cells with the GeneCaP formulations at 4° C., as well as 37° C.

The cells will also be placed into wells which had been pre-coated with thin layers of the polymerised "PolyGen-eCaP" and then pre-incubated (and partially degraded) for various periods (1 day-2 weeks), in culture medium at 37° C. Measurements will be made of cell attachment at 4 h and 24 h and subsequent cell growth (using the Quantokine flourescent assay), of cytotoxicity (trypan blue exclusion), of DNA uptake and then specific biological function, as discussed below. Additionally SEM (with EDAX) and Raman mapping microscopy will be used to examine cell attachment. In later experiments we will seek to confirm these findings with different types of cell obtained from other murine organs, eg liver, muscle, bone, although the long-term maintenance of such primary cultures is far more difficult than the fibroblast cells which are already available and which we will use primarily in this study.

d) GeneCaP Gene Function Optimisation

For studies of gene function with selected optimised formulations and culture conditions, a sensitive luciferase 'reporter' gene is first used to confirm the biological efficiency of this new in vitro DNA delivery system, by measuring the acquisition of luciferase activity by the normal cells. To determine the efficacy of enzyme 'correction' of the lysosomal disease specifically, we will use MCV cells (a fibroblast cell line derived from the MPS VII (GUS-deficient) mouse) together with a plasmid-derived cDNA coding for the normal murine GUS gene which is able to generate GUS enzyme activity. Increases in GUS activity after exposure to gene delivering suspensions will be measured in lysates of cultured cells using the fluorogenic substrate 4-methylumbelliferyl-β-D-glucuronide, while individual cells will also be monitored using the histological stain napthyl ASBI β-D-glucuronide. Using these assays, a limited number of formulations can be selected, on the basis of biological activity (ie DNA transfer and gene function), for in vivo experiments, as described below.

e) In vivo Investigations

The GUS-test system is tested in vivo using a murine model of MPS VII. Optimized GUS gene-containing and 'control' materials are injected into target organs (e.g. skin, spleen, liver, kidney) of the MPS VII mouse and GUS enzyme activity in various tissues will be measured as a function of time after administration and dose. Tissues will also be tested to confirm the simultaneous presence of DNA acquired from the composites using β-galactosidase reporter gene-material formulations and measuring β-galactosidase activity (with the X-gal substrate).

Example 7

Non-Degradable Antibacterial Composites/Adhesives for Tooth Repair a) Background and Summary Bacterial microleakage between a tooth and restoration has been described as the most significant risk in restorative dentistry. The present invention therefore further provides novel restorative composites/adhesives that release the antibacterial agent chlorhexidine (CHX).

It is known that release of CHX from dental composites and adhesives can prevent leakage of bacteria under a restoration (see Leung et at Biomaterials 26: 2005, 7143-7153). A major problem, however, is that to provide release the composites need to absorb water which in turn causes a decline in their strength. Through the use of the reactive fillers of the present invention water absorption can be combined with strong substantially non-degradable polymers to balance these requirements. In essence, unlike conventional composites which are generally based on Silica-based fillers, the reactive filler binds the water such that it is not available to cause plasticization and weaken the surrounding polymer. Additionally, calcium phosphates from the fillers may bind to the surrounding hydroxyapatite in tooth structure thereby improving adhesion and reducing gaps between the tooth and restoration through which the bacteria could penetrate.

b) Chlorhexidine Release, Water Sorption and Strength in Conventional Composites CHX release from and water sorption (determined from mass increase) was assessed in composites derived from different ratio's of the (co)monomers hydroxyethylmethacrylate (HEMA), triethyleneglycoldimethacrylate (TEGDMA) and urethanedimethacrylate (UDMA). HEMA is the more hydrophilic monomer, therefore is expected to increase water sorption.

Figure 18:
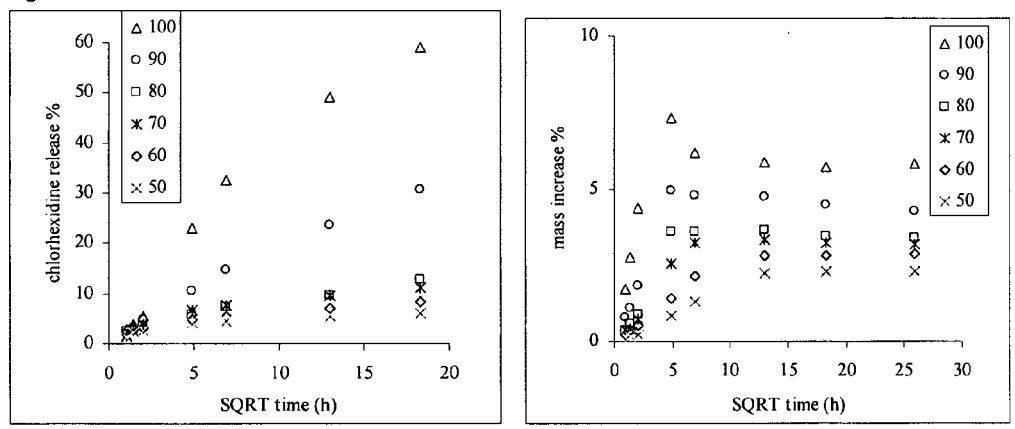
FIGS. 18a) and b): Chlorhexidine (CHX) release from, and water sorption by (determined from mass increase) conventional non-degradable composites derived from different ratio's of the (co)monomers hydroxyethylmethacrylate (HEMA), triethyleneglycoldimethacrylate (TEGDMA) and urethanedimethacrylate (UDMA).
FIG. 18c) shows the flexural strength of these composites. These composites contain a silane coated conventional fluoroaluminosilicate dental restorative filler. As the HEMA content and hydrophilicity increase water sorption and chlorhexidine release are raised but strength substantially decreased.
Figure 18:
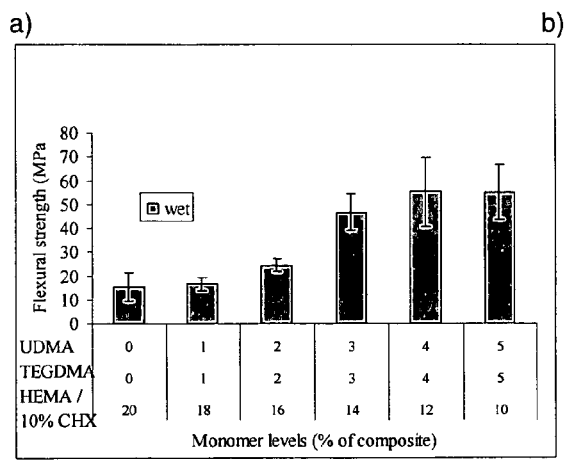

FIGS. 18a) and b) show the results of conventional composites based on Si fillers and containing 50 to 100% HEMA in the monomer phase showing that increase in hydrophilicity and decrease in crosslinking increases both properties. These composites also contain UDMA and TEGDMA in the monomer in equal amounts. The filler content is 80 wt % Fuji II LC glass and CHX level 10 wt % of the HEMA.

FIG. 18c) shows the flexural strength of the above composites prepared using conventional fillers after 24 hours in water. This shows a reduction in strength upon raising HEMA content, water sorption and CHX release.

c) Non-Degradable "Reactive Filler" Composites

Samples were prepared using a liquid phase composed of HEMA:TEGDMA:UDMA in the ratio 10:5:5 (i.e comparable with 50% HEMA in the monomer phase in FIGS. 18a) and b). The HEMA contains either 0 or 10% CHX. The monomers are combined with equal masses of bTCP and MCPM in powder liquid ratios (PLR) of 3:1 or 1:1. The minimum MCPM particle size is 20 or 75 micron. Samples (2 mm thick and 12 mm diameter discs) are stored in either water or buffer solution and CHX release determined using UV spectroscopy.

Figure 19:
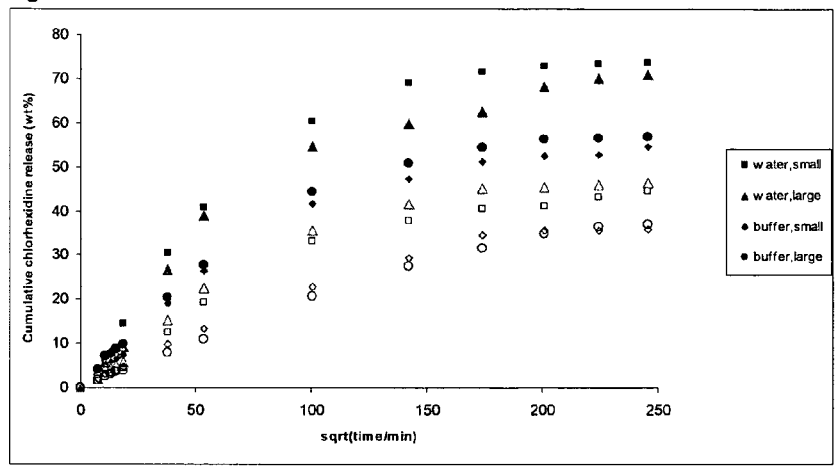
FIG. 19a): CHX release into deionised water or phosphate buffer solution versus the square root of time for non-degradable reactive filler composites containing either small or large MCPM particles and HEMA:UDMA:TEGDMA in the ratio 2:1:1. Filled and unfilled symbols refer to high and low reactive filler ratio respectively.
FIG. 19b) shows the averaged effects of powder liquid ratio (PLR, first 2 columns), MCPM particle size (next 2 columns), and type of storage solution (final 2 columns) on the mean total chiorhexidine release FIG. 19c) shows the mass increase versus square root of time for samples containing either small or large MCPM particles placed in deionised water or phosphate buffer solution. Filled and unfilled symbols refer to high and low reactive filler ratio (PLR 3:1 or 1:1) respectively.
FIG. 19d) shows the average maximum mass increases of various composites.
Figure 19:
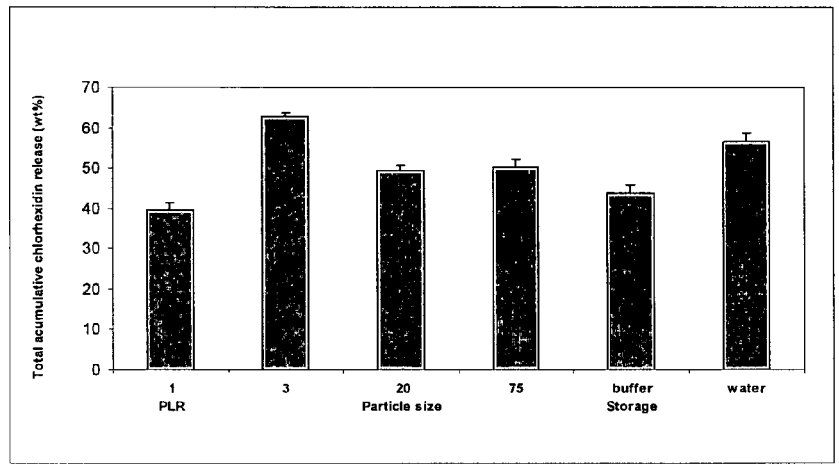
Figure 19:
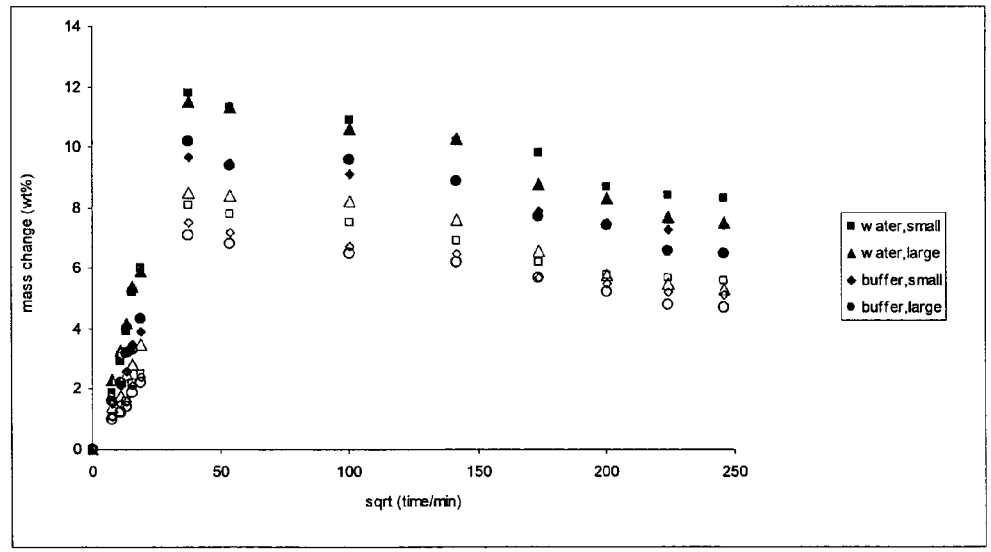
Figure 19:
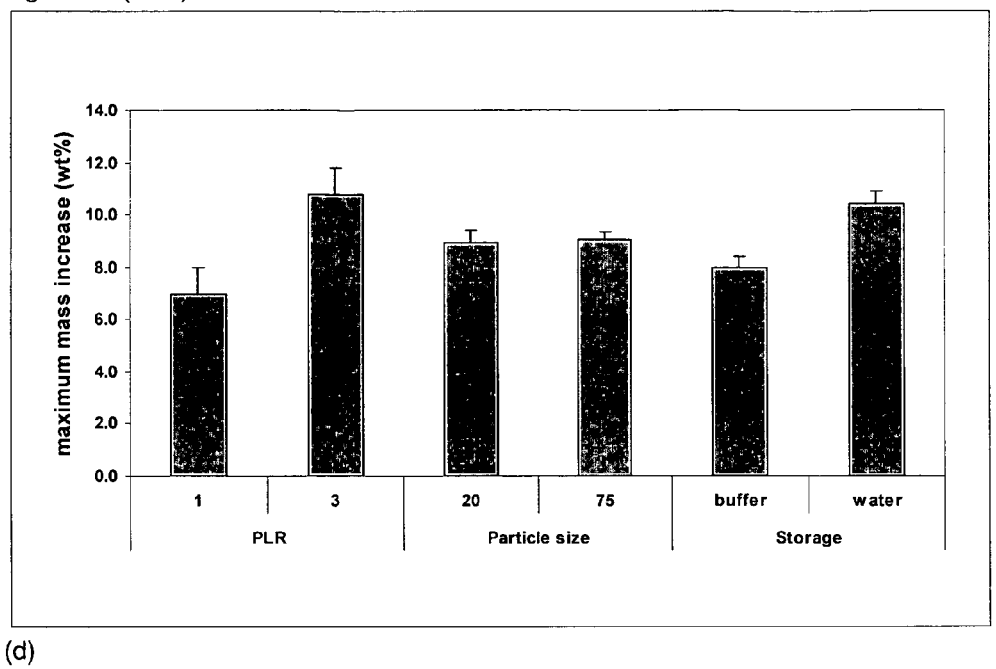

FIG. 19a) shows chlorhexidine release into deionised water or phosphate buffer solution versus the square root of time for samples containing either small or large MCPM particles. Filled and unfilled symbols refer to high and low reactive filler ratio respectively.

As can be seen, there can be significant (up to nearly 80% release) of the CHX.

FIG. 19b) shows the averaged effects of powder liquid ratio (PLR, first 2 columns), MCPM particle size (next 2 columns), and type of storage solution (final 2 columns) on the mean total chlorhexidine release The above results show that as the PLR is raised increased levels of chlorhexidine can be released from the dental restorative material. In composites containing non-reactive filler and the above monomers only 6% CHX can be released into water instead of nearly 80% with high MCPM+βTCP.

FIG. 19c) shows the mass increase versus square root of time for samples containing either small or large MCPM particles placed in deionised water or phosphate buffer solution. Filled and unfilled symbols refer to high and low reactive filler ratio (PLR 3:1 or 1:1) respectively.

FIG. 19d) shows the average maximum mass increases of the various composites. This shows that with higher PLR and in water instead of buffer, greater water sorption occurs which correlates with higher CHX release in FIG. 19b).

Figure 20:
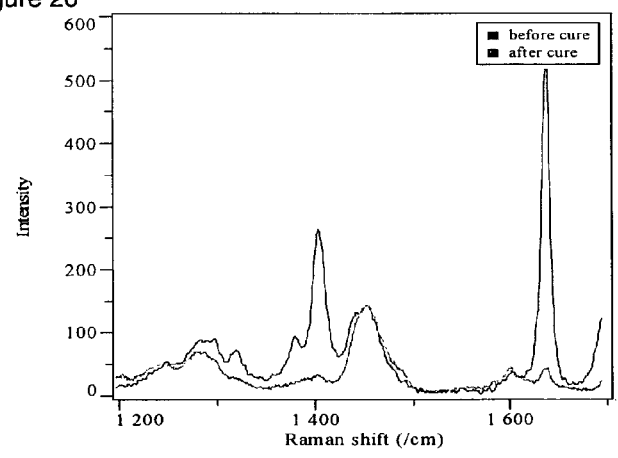
FIGS. 20a) and b): Raman spectra of non-degradable reactive filler composite samples of the invention prepared using HEMA:UDMA:TEGDMA in the ratio 2:1:1 .
Figure 20:
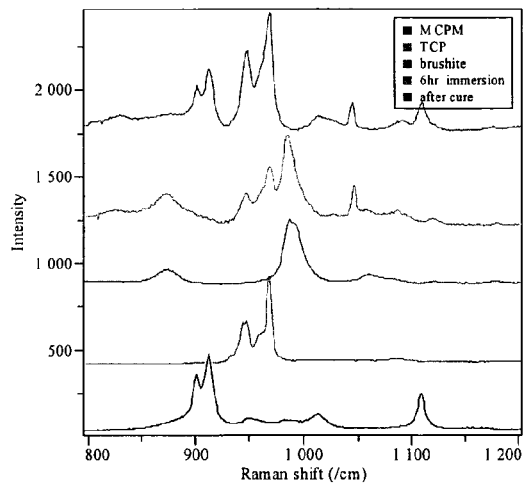

The presence of the reactive fillers of the invention does not inhibit polymerisation. This is shown in FIG. 20a) which shows representative raman spectra between 1200 and 1700 cm$^{-1}$ of a composite sample before after light exposure. It can be seen that the peak at 1640 due to a C=C group practically disappears.

Additionally, as discussed earlier, within the polymer the MCPM and bTCP react after water sorption to form brushite. This is shown in FIG. 20b) which shows a comparison of Raman spectra between 800 and 1200 cm$^{-1}$ of a composite sample after curing, followed by 6 hr immersion in deionised water with spectra of MCPM, β-TCP and brushite.

Figure 21:
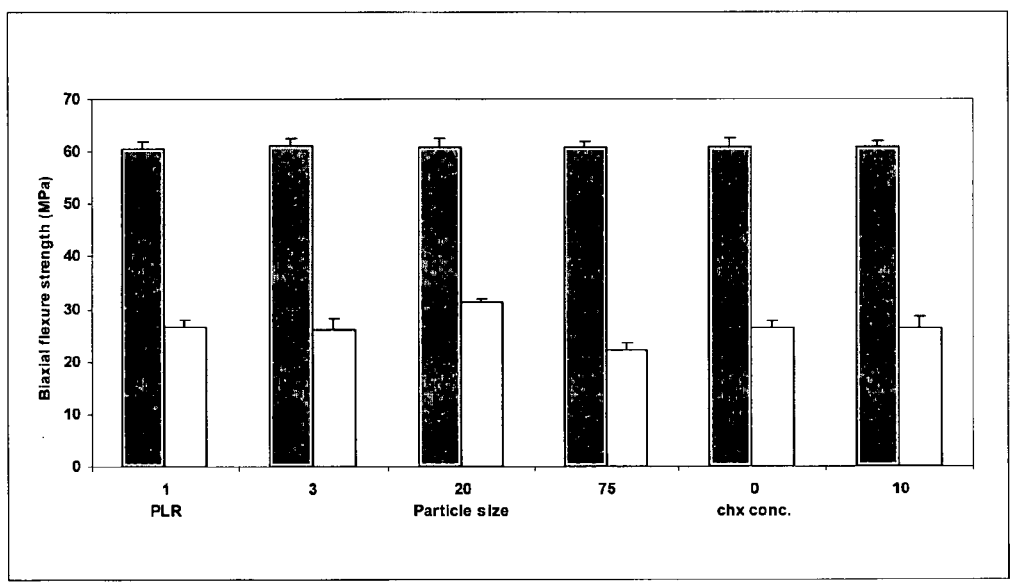
FIG. 21: Effects of varying filler mass fraction, MCPM particle size and adding chiorhexidine on biaxial flexure strength of dry and wet non-degradable reactive filler composite samples. Filled and unfilled bars refer to dry and wet samples respectively.

Finally FIG. 21 shows the effects of varying filler mass fraction, MCPM particle size and adding chlorhexidine on biaxial flexure strength of dry and wet composite samples. Filled and unfilled bars refer to dry and wet samples respectively. FIG. 21 shows that although water sorption by the composite does decrease the strength, if the particle size is small then flexural strength is still over 30 MPa. This compares with a value of only ~15 MPa for the above high CHX releasing HEMA/conventional filler composite.

Example 8

Reactive Fillers Can Reduce Cytotoxity of Polymers in Composites a) Materials and Methods
Aim This example assesses cytotoxicity of extracts from P17L4 composite formulations obtained with 6 h immersion in culture medium
Synthesis of Composite Samples Discs of 12 mm diameter and 2 mm depth were prepared as previously using P17L4. The filler was a mixture of 6TCP and MCPM in a 1:1 or 4:1 ratio. Powder:liquid ratios of 70:30 and 50:50 were used. The particles of MCPM had been ground and passed through sieves of 106, 75, 38 and 20 micron. Sample formulations based on factorial design are listed in Table 4. Each formulation has a duplicate. Controls include tissue culture plastic (TCP) without extract and extracts from the pure polymer P17L4 (sample C11) and intermediate formulations (C1 and C10).

TABLE 4

Composite formulations

| Sample No. | βTCP:MCPM (mol ratio) | Liquid mass fraction (%) | Particle size of MCPM (μm) |
|---|---|---|---|
| C1 | 2:1 | 40 | 38~75 |
| C2 | 4:1 | 30 | 75~106 |
| C3 | 4:1 | 50 | 20~38 |
| C4 | 4:1 | 50 | 75~106 |
| C5 | 4:1 | 30 | 20~38 |
| C6 | 1:1 | 50 | 75~106 |

TABLE 4-continued

Composite formulations

| Sample No. | βTCP:MCPM (mol ratio) | Liquid mass fraction (%) | Particle size of MCPM (μm) |
|---|---|---|---|
| C7 | 1:1 | 30 | 75~106 |
| C8 | 1:1 | 50 | 20~38 |
| C9 | 1:1 | 30 | 20~38 |
| C10 | 2:1 | 40 | 38~75 |
| C11 | N/A | 100 | N/A |

Preparation of Sample Extracts

Composite discs were sterilized by UV light (Steristrom 2537 Å, Coast-Air, London, UK) for 30 min, 15 min for each side and then soaked in 10 ml low glucose growth medium (Dulbecco's modified Eagle's medium with 4 mM L-glutamine supplemented with 10% fetal bovine serum, 50 IU/mL of penicillin and 50 μL/mL of streptomycin) at 37° C. for 6 h in a 15 ml centrifuge tube.
Cytotoxicity Assessment of Sample Extracts on MG 63 Cells MG 63 cell suspension of initial density of 10,000 cells/ml was added into a 96-well plate, 200 μl for each well, and incubated at 37° C. (5% $CO_2$, 70% humidity) for 4 h. After cell adhesion, the normal medium was replaced by the sample storage solutions obtained above for the 11 formulations. Each formulation has 6 replicates. The MG 63 cells were incubated in the sample extracts at 37° C. for 3 days at which time 20 μl of AlamarBlue indicator dye was added to each well. After a further 4 h incubation, 100 μl from each cell was removed and fluorescence due to the replicating cells measured using an excitation wavelength of 530 nm and emission wavelength of 590 nm.
b) Results FIG. 22a) shows the fluorescence due to MG 63 cell growth in sample extracts.

Figure 22:
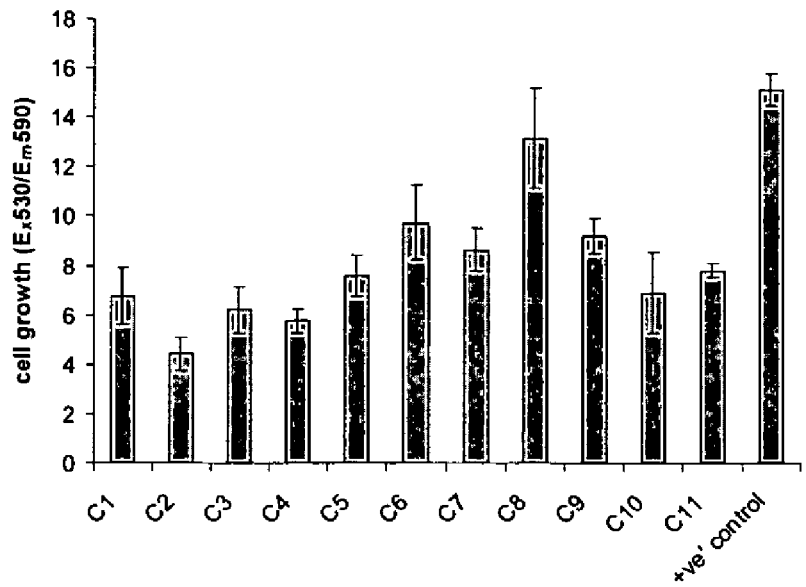
FIGS. 22a) and b): Effect on cell growth and hence cytotoxicity of extracts from degradable reactive filler materials prepared according to the present invention.
Figure 22:
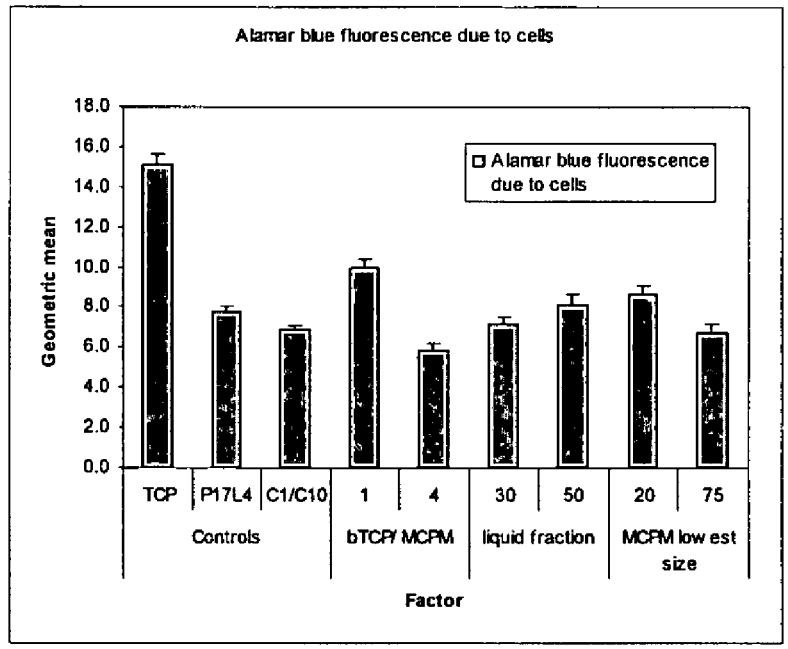

FIG. 22b) shows the geometric average fluorescence due to cells exposed to sample extracts (error bars are 95% confidence intervals).

The results in these Figures show that with bTCP and MCPM in a 1:1 molar ratio average cytotoxicity of the specimen extracts is reduced in comparison with that of the pure polymer P17L4. Smaller MCPM particle size also reduces extract cytotoxicity.

REFERENCES

1. Antonov E N, Bagratashvili V N, Whitaker M J, Barry J J A, Shakesheff K M, Konovalov A N et al. Three-dimensional bioactive and biodegradable scaffolds fabricated by surface-selective laser sintering. Advanced Materials 2005; 17:327.
2. Petzold R, Zeilhofer H-F, Kalender W A. Rapid prototyping technology in medicine-basics and applications. Computerized Medical Imaging and Graphics 1999; 23:277-84.
3. Popov V K, Evseev A V, Ivanov A L, Roginski W, Volozhin A I, Howdle S M. Laser stereolithography and supercritical fluid processing or custom-designed implant fabrication. Journal of Materials Science-Materials in Medicine 2004; 15:123-8.
4. Quick D J, Macdonald K K, Anseth K S. Delivering DNA from photocrosslinked, surface eroding polyanhydrides. Journal of Controlled Release 2004; 97:333-43.
5. Poshusta A K, Burdick J A, Mortisen D J, Padera R F, Ruehlman D, Yaszemski M J, Anseth K S. Histocompatibility of photocrosslinked polyanhydrides: A novel in situ 6. Burkoth A K, Burdick J, Anseth K S. Surface and bulk modifications to photocrosslinked polyanhydrides to control degradation behavior. Journal of Biomedical Materials Research 2000; 51:352-9.
7. Davis K A, Burdick J A, Anseth K S. Photoinitiated crosslinked degradable copolymer networks for tissue engineering applications. Biomaterials 2003; 24:2485-95.
8. Quick D J, Anseth K S. DNA delivery from photo-crosslinked PEG hydrogels: encapsulation efficiency, release profiles, and DNA quality. Journal of Controlled Release 2004; 96:341-51.
9. Fisher J P, Tirnmer M D, Holland T A, Dean D, Engel P S, Mikos A G. Photoinitiated cross-linking of the biodegradable polyester polypropylene fumarate). Part I. Determination of network structure. Biomacromolecules 2003; 4:1327-34.
10. Lyu S, Sparer R, Untereker D. Analytical solutions to mathematical models of the surface and bulk erosion of solid polymers. Journal of Polymer Science Part B-Polymer Physics 2005; 43:383-97.
11. Debnath S, Ranade R, Wunder S L, McCool J, Boberick K, Baran G. Interface effects on mechanical properties of particle-reinforced composites. Dental Materials 2004; 20:677-86.
12. Niemela T. Effect of [beta], tricalcium phosphate addition on the in vitro degradation of self-reinforced poly-l,d-lactide. Polymer Degradation and Stability 2005; 89:492-500.
13. Wolfe M S, Dean D, Chen J E, Fisher J P, Han S H, Rimnac C M, Mikos A G. In vitro degradation and fracture toughness of multilayered porous poly(propylene fumarate)/beta-tricalcium phosphate scaffolds. Journal of Biomedical Materials Research 2002; 61:159-64.
14. Urayama H, Ma C H, Kimura Y. Mechanical and thermal properties of poly(L-lactide) incorporating various inorganic fillers with particle and whisker shapes. Macromolecular Materials and Engineering 2003; 288:562-8.
15. Hasegawa S, Ishii S, Tamura J, Furukawa T, Neo M, Matsusue Y et al. A 5-7 year in vivo study of high-strength hydroxyapatite/poly(L-lactide) composite rods for the internal fixation of bone fractures. Biomaterials 2006; 27:1327-32.
16. Tsunoda M. Degradation of poly (DL-lactic acid-co-glycolic acid) containing calcium carbonate and hydroxyapatite fillers—Effect of size and shape of the fillers. Dental Materials Journal 2003; 22:371-82.
17. Li H Y, Chang J. pH-compensation effect of bioactive inorganic fillers on the degradation of PLGA. Composites Science and Technology 2005; 65:2226-32.
18. Oh K S, Choi H W, Kim S R. Temperature rise and setting of beta-TCP-MCPM bone cement containing dense beta-TCP granules. Current Applied Physics 2005; 5:489-92.
19. Hofmann M P, Gbureck U, Grover L M, Barralet J E. Stearate salts as brushite bone cement setting retardants. Key Engineering Materials, 2005:19-22.
20. Stanczyk M. Study on modelling of PMMA bone cement polymerisation. Journal of Biomechanics 2005; 38(7):1397-1403.
21. Stanczyk M, van Rietbergen B. Thermal analysis of bone cement polymerisation at the cement-bone interface. Journal of Biomechanics 2004; 37(12):1803-1810.
22. Lohmann C H, Dean D D, Koster G, Casasola D, Buchhorn G H, Fink U et al. Ceramic and PMMA particles differentially affect osteoblast phenotype. Biomaterials 2002; 23(8):1855-1863.
23. Burkhart S S. The evolution of clinical applications of biodegradable implants in arthroscopic surgery. Biomaterials 2000; 21(24):2631-2634.
24. Ho S M, Young A M. Synthesis, polymerisation and degradation of poly(lactide-co-propylene glycol) dimethacrylate adhesives. European Polymer Journal 2006; 42(8):1775-1785.
25. Kim B S, Hrkach J S, Langer R. Biodegradable photo-crosslinked poly(ether-ester) networks for lubricious coatings. Biomaterials 2000; 21(3):259-265.
26. Kumar N, Langer R S, Domb A J. Polyanhydrides: an overview. Advanced Drug Delivery Reviews 2002; 54(7):889-910.
27. Timmer M D, Ambrose C G, Mikos A G. In vitro degradation of polymeric networks of poly(propylene fumarate) and the crosslinking macromer poly(propylene fumarate)-diacrylate. Biomaterials 2003; 24(4):571-577.
28. Schmitz J P, Hollinger J O, Milam S B. Reconstruction of bone using calcium phosphate bone cements: A critical review. Journal of Oral and Maxillofacial Surgery 1999; 57(9):1122-1126.
29. Wolff K D, Swaid S, Nolte D, Bockmann R A, Holzle F, Muller-Mai C. Degradable injectable bone cement in maxillofacial surgery: indications and clinical experience in 27 patients. Journal of Cranio-Maxillofacial Surgery 2004; 32(2):71-79.
30. Ginebra M P, Traykova T, Planell J A. Calcium phosphate cements as bone drug delivery systems: A review. Journal of Controlled Release 2006; 113(2):102-110.
31. Tanimoto Y, Nemoto K. Influence of particle size of fillers on frictional wear of dental composite resins. Composite Interfaces 2004; 11(1):15-24.
32. Atai M, Watts D C, Atai Z. Shrinkage strain-rates of dental resin-monomer and composite systems. Biomaterials 2005; 26(24):5015-5020.
33. Weniger K, Helfmann J, Muller G. Penetration depth of light for argon laser curing of dental composites. Medical Laser Application 2005; 20(1):71-76.
34. Majekodunmi A O, Deb S, Nicholson J W. Effect of molecular weight and concentration of poly(acrylic acid) on the formation of a polymeric calcium phosphate cement. Journal of Materials Science-Materials in Medicine 2003; 14(9):747-752.
35. Bohner M, Lemaitre J, VanLanduyt P, Zambelli P Y, Merkle H P, Gander B. Gentamicin-loaded hydraulic calcium phosphate bone cement as antibiotic delivery system. Journal of Pharmaceutical Sciences 1997; 86(5):565-572.
36. Ferreira F, Vaz M A, Simoes J A. Mechanical properties of bovine cortical bone at high strain rate. Materials Characterizationln Press, Uncorrected Proof.
37. Kotha S P, Guzelsu N. Tensile behavior of cortical bone: Dependence of organic matrix material properties on bone mineral content. Journal of Biomechanics In Press, Corrected Proof.
38. Wang T, Feng Z. Dynamic mechanical properties of cortical bone: The effect of mineral content. Materials Letters 2005; 59:2277-80.
39. Temenoff J S, Mikos A G. Injectable biodegradable materials for orthopedic tissue engineering. Biomaterials 2000; 21:2405-12.
40. Ural E, Kesenci K, Fambri L, Migliaresi C, Piskin E. Poly(,-cactide/[var epsilon]-caprolactone)/hydroxyapatite composites. Biomaterials 2000; 21:2147-54.
41. He S L, Yaszemski M J, Yasko A W, Engel P S, Mikos A G. Injectable biodegradable polymer composites based on poly(propylene fumarate) crosslinked with poly(ethylene glycol)-dimethacrylate. Biomaterials 2000; 21:2389-94.

42. Bohner M. Calcium orthophosphates in medicine: from ceramics to calcium phosphate cements. Injury-International Journal of the Care of the Injured 2000; 31:S37-S47.

43. Grover L M, Gbureck U, Young A M, Wright A J, Barralet J E. Temperature dependent setting kinetics and mechanical properties of beta-TCP-pyrophosphoric acid bone cement. Journal of Materials Chemistry 2005; 15:4955-62.

44. Viala S, Freche M, Lacout J L. Preparation of a new organic-mineral composite: Chitosan-Hydroxyapatite. Annales de Chimie Science des Materiaux 1998; 23:69-72.

45. Tortet L, Gavarri J R, Nihoul G, Dianoux A J. Proton mobilities in brushite and brushite/polymer composites. Solid State Ionics 1997; 97:253-6.

46. Onoda A, Doi M, Takahashi K, Okamura T, Yamamoto H, Ueyama N. Solid state P-31 MAS NMR detection of hydrogen-bonded phosphate polymer in calcium-phosphate composites. Chemistry Letters 2004; 33:466-7.

47. Flautre B, Lemaitre J, Maynou C, Van Landuyt P, Hardouin P. Influence of polymeric additives on the biological properties of brushite cements: an experimental study in rabbit. Journal of Biomedical Materials Research Part A 2003; 66A:214-23.

48. Reed C S, TenHuisen K S, Brown P W, Allcock H R. Thermal stability and compressive strength of calcium-deficient hydroxyapatite poly[bis(carboxylatophenoxy)phosphazene] composites. Chemistry of Materials 1996; 8:440-7.

The invention claimed is:

1. A process for production of a composite material comprising the steps of:
    i) providing a fluid formulation comprising (1) at least one compound capable of polymerisation and/or cross-linking and (2) a water-consuming reactive filler;
    ii) optionally injecting said formulation into a site of use;
    iii) polymerising and/or cross-linking said compound, to form a solid polymer matrix;
    iv) causing or allowing said filler to react with water absorbed by said polymer matrix, to produce a solid filler material which is dispersed throughout the composite material,
        wherein the reactive filler comprises a first calcium-containing compound and a second inorganic compound, which is a phosphate-containing compound, said first and second components reacting with each other to form the reactive filler which reacts with water.

2. A process as claimed in claim 1 wherein the formulation further comprises one or more of the following additives: a polymerisation initiator; diluent monomers; hydroxyquinone; a protein to encourage cell adhesion; an active ingredient,
    which active ingredient is optionally selected from: DNA; an antibacterial agent; an antifungal agent; an anti-inflammatory agent; an analgesic.

3. A process as claimed in claim 1 wherein the reactive filler optionally makes up greater than 50%, by weight of the formulation.

4. A process as claimed in claim 1 wherein reaction of the reactive filler with water consumes preferably at least 90% of the water absorbed into the polymer matrix.

5. A process as claimed in claim 1 wherein the calcium-containing compound is selected from the list consisting of: α or β tricalcium phosphate (TCP); dicalcium phosphate; dicalcium phosphate dihydrate (brushite); calcium dihydrogen phosphate; monocalcium phosphate monohydrate (MCPM); tetracalcium phosphate; α, β or γ calcium pyrophosphate.

6. A process as claimed in claim 1 wherein the reactive filler undergoes a reaction with water which consumes at least one, two, three, four, five or six moles, or seven moles of water per mole of filler.

7. A process as claimed in claim 5 wherein the reactive filler is a mixture of β-TCP and MCPM, optionally in a 1:1 molar ratio, which combine when mixed with water to form brushite.

8. A process as claimed in claim 1 wherein the reactive filler is provided as particles in the range of 0.5 to 200 μm in size.

9. A process as claimed in claim 1 wherein the compound capable of polymerisation and/or cross-linking is present as a non-aqueous fluid phase.

10. A process as claimed in claim 1 wherein the compound capable of polymerisation and/or cross-linking is capable of cross-linking and is selected from the list: a poly(ether-co-ester) dimethacrylate (which is optionally a poly(lactide-co-propylene glycol-co-lactide)dimethacrylate); a polyanhydride forming monomer; a polypropylene fumarate: in each case bearing polymerisable (meth)acrylate or vinyl groups optionally on the chain ends.

11. A process as claimed in claim 1 wherein:
    (i) the compound capable of polymerisation and/or cross-linking forms a solid polymer matrix which is degradable,
        and the solidified polymer matrix which is degradable is selected from: a poly(ether-co-ester); a cross-linked polyanhydride; a polyorthoester; a polycyanoacrylate; a polysaccharide; a protein,
        and wherein the compound capable of polymerisation and/or cross-linking is optionally a triblock dimethacrylate with a central polypropylene glycol (PPG) section of molecular weight 400 to 2000 g/mol, capped at both ends with lactide segments (LA) with between 2 and 8 lactic acid units and further bearing two or more (meth)acrylate groups on the chain ends, or
    (ii) the compound capable of polymerisation and/or cross-linking forms a solid polymer matrix which is non-degradable,
        and the compound capable of polymerisation and/or cross-linking is optionally selected from: (meth)acrylate monomers including, methylmethacrylate, acrylic acid, hydroxyethylmethacrylate (HEMA), urethane dimethacrylate (UDMA), triethyleneglycol dimethacrylate (TEGDMA).

12. A method of bone repair or of fixation of a dental or surgical implant into a cavity or location, which method comprises performing the process of claim 1, wherein:
    (i) the fluid formulation is injected into the site of bone damage or the cavity or location respectively;
    (ii) polymerising and/or cross-linking said compound is performed by curing said formulation to form a composite material which is adhered to the damaged bone or said dental or surgical implant respectively;
    (iii) degradation of said composite material causes concomitant growth of new bone tissue.

13. A method for providing a dental composite or dental or surgical implant at a cavity or location, which method comprises performing the process of claim 1, wherein:
    (i) the fluid formulation is injected into the cavity or location; and
    (ii) polymerising and/or cross-linking said compound is performed by curing said formulation to form a composite material which is adhered to said dental cavity or dental or surgical implant.

14. A method as claimed in claim 13 wherein the implant is a membrane for guided tissue regeneration and the solid polymer matrix is degradable.

15. A method as claimed in claim 13 wherein in the dental composite the solid polymer matrix is non-degradable.

16. A method as claimed in claim 15 wherein the fluid formulation comprises a mixture of reactive filler and non-reactive filler, which non-reactive filler is optionally silica based.

17. A method of delivery of an active agent, which method comprises performing the process of claim 1, wherein:
   (i) the fluid formulation comprises an active agent;
   (ii) the fluid formulation is injected into a site of use;
   (iii) reaction of the reactive filler with water absorbed into the polymer matrix and/or degradation of said composite material causes concomitant release of said active agent.

18. A method as claimed in claim 17 wherein the active agent is an antibacterial agent.

19. A method as claimed in claim 18 wherein the antibacterial agent is chlorhexidine.

20. A method as claimed in claim 18 wherein the site of use is the periodontal pocket.

21. A method as claimed in claim 17 wherein the active agent is DNA, and wherein said DNA is present within water droplets dispersed within the fluid formulation.

22. A kit for producing a fluid formulation and/or a composite material:
   (a) at least one compound capable of polymerising and/or cross-linking to form a solid polymer matrix;
   (b) a water-consuming reactive filler, capable of reaction with water absorbed into the polymer matrix to produce a solid material;
   (c) optionally an active agent for delivery; and
   (d) optionally written instructions for combining said compound and said filler and curing them,
   wherein the reactive filler comprises a first calcium-containing compound and a second inorganic compound, which is a phosphate-containing compound, said first and second components reacting with each other to form the reactive filler which reacts with water.

23. A process as claimed in claim 1 wherein:
   (i) the fluid formulation is injected into a site of bone damage or a cavity or location into which a dental or surgical implant is to be fixed;
   (ii) polymerising and/or cross-linking said compound is performed by curing said formulation to form a composite material which is adhered to the damaged bone or said dental or surgical implant, respectively,
   (iii) degradation of said composite material causes concomitant growth of new bone tissue.

* * * * *